(12) United States Patent
Johnson et al.

(10) Patent No.: US 10,809,222 B2
(45) Date of Patent: Oct. 20, 2020

(54) OPIOID DETECTION BASED ON HIGH QUALITY GRAPHENE TRANSISTOR ARRAYS AND A SYNTHETIC MU RECEPTOR

(71) Applicant: The Trustees of The University of Pennsylvania, Philadelphia, PA (US)

(72) Inventors: Alan T. Johnson, Philadelphia, PA (US); Jin Xi, Media, PA (US); Ganghee Han, Philadelphia, PA (US); Mitchell Lerner, Philadelphia, PA (US); Jeffery G. Saven, Philadelphia, PA (US); Renyu Liu, Media, PA (US); Felipe Matsunaga, Olmsted Township, OH (US); Jose Manuel Perez-Aguilar, New York, NY (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/786,674

(22) PCT Filed: Apr. 25, 2014

(86) PCT No.: PCT/US2014/035490
§ 371 (c)(1),
(2) Date: Oct. 23, 2015

(87) PCT Pub. No.: WO2014/176524
PCT Pub. Date: Oct. 30, 2014

(65) Prior Publication Data
US 2016/0123919 A1    May 5, 2016

Related U.S. Application Data

(60) Provisional application No. 61/815,934, filed on Apr. 25, 2013, provisional application No. 61/815,939, filed on Apr. 25, 2013.

(51) Int. Cl.
*G01N 27/327* (2006.01)
*G01N 33/543* (2006.01)
(Continued)

(52) U.S. Cl.
CPC ......... *G01N 27/3275* (2013.01); *C23C 16/44* (2013.01); *G01N 27/4145* (2013.01);
(Continued)

(58) Field of Classification Search
CPC ........... G01N 27/3275; G01N 27/4145; G01N 27/4166; G01N 33/9486; G01N 33/54373; C23C 16/44
See application file for complete search history.

(56) References Cited

U.S. PATENT DOCUMENTS 6,225,080 B1 * 5/2001 Uhl ...................... C07K 14/705
                                                         435/252.3
9,091,640 B1 * 7/2015 Mohapatra ........... G01N 27/307
(Continued)

FOREIGN PATENT DOCUMENTS

| EP | 2426487 A1 | 3/2012 |
|---|---|---|
| WO | 2012/112746 | * 8/2012 |
| WO | WO 2012/112746 A1 | 8/2012 |

OTHER PUBLICATIONS

Rudikoff et al., Single amino acid substitution altering antigen-binding specificity, 1982, Procedings of the National Academy of Sciences of the USA, vol. 79, pp. 1979-1983. (Year: 1982).*
(Continued)

*Primary Examiner* — Melanie Brown
(74) *Attorney, Agent, or Firm* — BakerHostetler

(57) ABSTRACT

The present invention provides methods for fabricating field-effect devices and sensor arrays. The field of the invention also pertains to methods of using the sensors individually, in combination, and in array fashion to detect
(Continued)

molecules. The present invention also provides for products produced by the methods of the present invention and for apparatuses used to perform the methods of the present invention.

7 Claims, 25 Drawing Sheets

Specification includes a Sequence Listing.

(51) Int. Cl.
*C23C 16/44* (2006.01)
*G01N 27/414* (2006.01)
*G01N 27/416* (2006.01)
*G01N 33/94* (2006.01)

(52) U.S. Cl.
CPC ... *G01N 27/4166* (2013.01); *G01N 33/54373* (2013.01); *G01N 33/9486* (2013.01); *G01N 2333/726* (2013.01)

(56) References Cited

U.S. PATENT DOCUMENTS

| | | | | |
|---|---|---|---|---|
| 9,146,209 | B2* | 9/2015 | Johnson | G01N 27/3278 |
| 2003/0013137 | A1* | 1/2003 | Barak | C12N 15/1089 435/7.21 |
| 2007/0196870 | A1* | 8/2007 | Perez | G01N 33/56966 435/7.2 |
| 2011/0214189 | A1 | 9/2011 | Gaitanaris et al. | |
| 2012/0214172 | A1* | 8/2012 | Chen | G01N 27/4146 435/6.19 |
| 2012/0220053 | A1* | 8/2012 | Lee | H01L 29/4908 436/501 |
| 2012/0252719 | A1 | 10/2012 | Zhang et al. | |
| 2012/0270230 | A1 | 10/2012 | Henderson et al. | |
| 2012/0301953 | A1* | 11/2012 | Duan | B82Y 30/00 435/287.9 |
| 2013/0018599 | A1* | 1/2013 | Peng | B82Y 15/00 702/30 |
| 2013/0306934 | A1* | 11/2013 | Lee | B82Y 15/00 257/12 |
| 2015/0038378 | A1* | 2/2015 | Cheng | G01N 33/5438 506/39 |
| 2015/0299852 | A1* | 10/2015 | Ozkan | B82Y 10/00 136/255 |

OTHER PUBLICATIONS

Chen et al. Noncovalent Sidewall Functionalization of Single-Walled Carbon Nanotubes for Protein Immobilization, J. Am. Chem. Soc. vol. 123, pp. 3838-3839 (Year: 2001).*
Tanaka, Chapter 1 Classification of Carbon, Carbon Nanotubes and Graphene 2nd edition, pp. 1-5. (Year: 2014).*
Raidongia et al., Chapter 14 Graphene Oxide: Some new Insights into and Old Material, Carbon Nanotubes and Graphene 2nd edition, pp. 341-373. (Year: 2014).*
Cui, et al., "NMR Structure and Dynamics of a Designed Water-Soluble Transmembrane Domain of Nicotinic Acetylcholine Receptor", Biochimica et Biophysica Acta, 2012, 617-626.
Lerner, et al., "Detecting Lyme Disease Using Antibody-Functionalized Single-Walled Carbonnanotube Transistors", Biosensors Bioelectron, Feb. 2013, 45, 163-167.
Liu, et al., "Biocompatible Graphene Oxide-Based Glucose Biosensors", Langmuir, Mar. 2010, 26(9):6158-60.
Lluis, et al., "Protein Engineering Methods Applied to Membrane Protein Targets", Protein Engineering Design & Selection, Oct. 2012, 91-100.
Manglik, et al., "Crystal Structure of the Mu-Opioid Receptor Bound to a Morphinan Antagonist", Nature, 2012, 485(7398), 321-6.
Navratilova, et al., "Screening for GPCR Ligands Using Surface Plasmon Resonance", ACS Med. Chem. Lett. 2011, 2(7):549-554.
Saito, et al., "Rama Spectroscopy of Graphene and Carbon Nanotubes", Advances in Physics, May 2011, vol. 60(3), 413-550.
Slovic, et al. "Computational Design of Water-Soluble Analogues of the Potassium Channel KcsA", PNAS, Feb. 2004, vol. 101(7), 1828-1833.
Slovic, et al., "Computational Design of a Water-Soluble Analog of Phospholamban", Protein Sciene, 2003, 337-348.
Szunerits, et al. "Recent Advances in the Development of Graphene-Based Surface Plasmon Resonance (SPR) Interfaces", Anal Bioanal Chem., Jan. 2013, 405(5),1435-43.
Veerapandian, et al., "Functionalized Graphene Oxide for Clinical Glucose Biosensing in Urine and Serum Samples", Int. Journ. of Nanomedicine, 2012, 6123-6136.
Yamazaki, et al., "GR-ThP5 Effects of an Interfacial Water Layer on Protein Absorption le Graphene Sheets on Solid Substrates", Thursday Afternoon Poster Session, 2012, 26-27.
Zhang, et al. Interactions of graphene and graphene oxide with proteins and peptides, Nanotechnology Reviews ePub Feb. 2013, 2(1 ): 27-45.
Lerner et al. "Scalable Production of Highly Sensitive Nanosensors Based on Graphene Functionalized with a Designed G Protein-Coupled Receptor", Nano Letters, May 14, 2014, vol. 14, No. 5, 2709-2714.
Pumera et al., "Graphene in biosensing", Materials Today, Jul. 1, 2011, vol. 14, Issues 7-8, 308-315.
Ye et al., "Graphene-protein bioelectronics devices with wavelength-dependent photoresponse", Applied Physics Letters, Jan. 16, 2012, vol. 100, No. 3, 12 pages.
Perez-Aguilar, et al., "A Computationally Designed Water-Soluble Variant of a G-Protein-Coupled Receptor: The Human Mu Opioid Receptor. PLoS One", Jun. 2013, vol. 8(6), 1-10.
Ma, et al., "NMR Studies of a Channel Protein Without Membranes: Structure and Dynamics of Water-Solubilized KcsA", Proc Natl Acad Sci, 2008, vol. 105(43), 16537-42.
Crasto, "Hydrophobicity Profiles in G Protein-Coupled Receptor Transmembrane Helical Domains", J. Receptor Ligand Channel Res., 2010, vol. 3, 123-133.
Kodali et al.,"Nonperturbative Chemical Modification of Graphene for Protein Micropattering", Dec. 23, 2010, Langmuir, vol. 27, No. 3, 863-865.
Chen et al., "Noncovalent sidewall functionalization of single-walled carbon nanotubes for protein immunolization", Jan. 1, 2001, Journal of the American Chemical Society, vol. 123, No. 16, 3838-3839.
Ohno et al., "Label-Free Aptamer-Based Immunoglobulin Sensors Using Graphene Field-Effect Transistors", Jul. 1, 2011, Japanese Journal of Applied Physics, vol. 50, No. 7, 070120.

* cited by examiner

FIG. 9

| Surface functional groups | Protein functional groups | Product |
|---|---|---|
| NHS ester | $H_2NR$ | amide |
| aldehyde | $H_2NR$ | imine |
| isothiocyanate | $H_2NR$ | thiourea |
| epoxide | $H_2NR$ | aminoalcohol |
| amine | $HO(O)CCH_2R$ | amide |

FIG. 12A
FIG. 12B
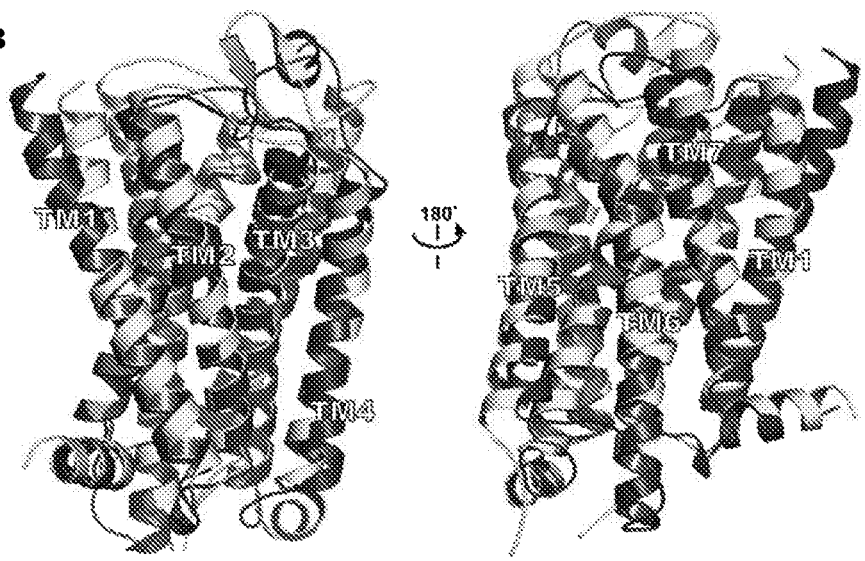
FIG. 12C

FIG. 15

|  | H | G | D | I |
|---|---|---|---|---|
| BOTTOM | 1416 | 1724 | 1345 | 1323 |
| TOP | 2400 | 2458 | 2498 | 2473 |
| LOGEC50 | -5.696 | -5.964 | -6.001 | -5.883 |
| HILLSLOPE | -5.524 | -16.56 | -5.235 | -13.44 |
| EC50 | 2.0128e-006 | 1.0854e-006 | 9.9732e-007 | 1.3084e-006 |

OPIOID DETECTION BASED ON HIGH QUALITY GRAPHENE TRANSISTOR ARRAYS AND A SYNTHETIC MU RECEPTOR

CROSS REFERENCE TO RELATED APPLICATIONS

This application is a National Stage Application filed under 35 U.S.C. 371 of International Application No. PCT/US2014/035490, filed Apr. 25, 2014, which claims priority to U.S. Provisional Patent Application No. 61/815,934, "Opioid Detection Based On High Quality Graphene Transistor Arrays And A Synthetic Mu Receptor," filed on Apr. 25, 2013, and U.S. Provisional Patent Application No. 61/815,939, "Water Soluble G Coupled Protein Receptor," filed Apr. 25, 2013, the entirety of which applications are incorporated herein for any and all purposes.

GOVERNMENT RIGHTS

This invention was made with government support under Grant Number NSF NSEC DMR08-32802 awarded by the National Science Foundation (Nano-Bio Interface Center) and under Grant Number K08-GM-093115-01 awarded by the National Institutes of Health. The government has certain rights in the invention.

FIELD OF THE INVENTION

The disclosed invention is in the field of chemical sensors. The invention also relates to the field of field-effect devices and sensor arrays and methods of manufacturing such devices and arrays. The field of the invention also pertains to methods of using the sensors individually, in combination, and in array fashion to detect molecules.

BACKGROUND OF THE INVENTION

Graphene has attracted much attention due to its superior electrical, mechanical, and optical properties. But there remain long-standing challenges to fabricating devices that maintain the unique electrical properties of high quality graphene. A solution to these problems would open the door for many applications of graphene field effect transistors ("GFET"s) in commercial markets and scientific research.

G-protein-coupled receptors (GPCRs) are an important group of transmembrane proteins involved in activating intracellular signal transduction pathways in response to an outside stimulus. GPCRs bind a variety of target ligands, from small molecules to large proteins. They are involved in a number of diseases, and as such are believed to be the target of approximately 40% of all modern pharmaceuticals. Mu-opioid receptors are a type of GPCR with a high binding affinity for opioids. Normally, GPCRs are unstable when removed from their native membrane, resulting in denaturation and loss of functionality. But by replacing exterior, non-ligand binding amino acids with more hydrophilic residues, GPCRs can be made more stable outside of the membrane.

Accordingly, there is a need for chemical sensors having fast all-electronic readout which are inexpensive to implement and compatible with modern technologies for data recording and analysis. There is also a need for chemical sensors having signal-to-noise ratios to allow for lower detection limits.

SUMMARY OF THE INVENTION

In meeting the described challenges, the present invention provides methods for detecting the presence of an analyte and/or determining analyte concentration in a sample, comprising applying a voltage to a graphene field effect transistor sensor having a conduction channel and comprising a detection molecule being bound by an amide bond to the graphene, measuring a current of the sensor, exposing the conduction channel to the sample, measuring the current of the sensor, determining the presence and concentration of analyte based upon a difference in the current, and determining the conformational changes of the detection molecule upon analyte binding.

The present invention provides methods for fabricating a sensing device, comprising effecting deposition of a graphene layer over a top surface of a metal catalyst foil having a top surface and a bottom surface, selectively depositing a gold layer over regions of the graphene layer, spin-coating the top surface of the foil having graphene and gold layers with a layer of PMMA, baking the foil, separating the PMMA and graphene from the foil with the gold-covered regions of graphene remaining on the foil, transferring the layer of PMMA with patterned graphene on it to a substrate having pre-fabricated electrodes such that the graphene places the prefabricated electrodes into electronic communication with one another, and removing the layer of PMMA.

The present invention provides methods for functionalizing a graphene field effect transistor having a graphene layer, comprising exposing the graphene layer to a solution of carboxylated diazonium salt to create carboxylate groups on the graphene layer, activating the carboxylate groups with a carbodiimide, stabilizing the carboxylate groups with NHS molecules, and displacing the NHS molecules with detection molecules having an accessible amine group so as to create an amide bond between the graphene layer and the receptor molecules.

The present invention provides methods for fabricating a sensing device, comprising disposing a graphene portion on an insulating substrate, the disposing being performed such that the graphene portion places two electrodes into electronic communication with one another, and linking a detection molecule to the graphene portion.

The present invention features sensing devices comprising a graphene portion placing first and second electrodes into electronic communication with one another, the graphene portion comprising a detection molecule bonded thereto, the detection molecule being in electronic communication with the graphene, and the detection molecule being capable of complementary binding to at least one target.

The present invention provides methods for detecting ligand binding to a functionalized graphene layer, comprising measuring a first G peak position in a Raman spectrum of the graphene layer, exposing the functionalized graphene layer to a fluid or gas containing ligands, and measuring a second G peak position in a Raman spectrum of the graphene layer.

The present invention provides methods for detecting ligand binding to a functionalized graphene layer, comprising measuring a first 2D peak position in a Raman spectrum of the graphene layer, exposing the functionalized graphene layer to a fluid or gas containing ligands, and measuring a second 2D peak position in a Raman spectrum of the graphene layer.

The present invention provides methods for determining analyte concentration in a sample, comprising applying a voltage to a graphene field effect transistor sensor having a conduction channel and comprising a detection molecule being bound by an amide bond to the graphene, measuring a first G peak, a first 2D peak, or both, of the sensor, exposing the conduction channel to the sample, measuring a second G peak, a second 2D peak, or both, of the sensor, and determining a concentration of analyte based upon a difference between the first G peak, the first 2D peak, or both, and the second G peak, the second 2D peak, or both.

The present invention provides methods of functionalizing a graphene field effect transistor having a graphene layer, comprising exposing the graphene layer to a first molecule so as to form pi-pi stacking bonds between a portion of the first molecule and the graphene layer, and displacing a portion of the first molecule via a displacement reaction so as to form a covalent bond between the graphene layer and a detection molecule.

The present invention provides methods of detecting the presence of an analyte and/or determining analyte concentration in a sample, comprising applying a voltage to a graphene field effect transistor sensor having a conduction channel and comprising a detection molecule being bound to the graphene, exposing the conduction channel to the sample, measuring a current of the sensor, and determining the presence, concentration, or both of the analyte based upon the current.

The present invention provides methods of functionalizing a graphene field effect transistor having a graphene layer, comprising exposing the graphene layer to 1-pyrene butanoic acid succinimidyl ester molecules having pyrene portions and NHS ester portions to create pi-pi stacking bonds between the pyrene portion and the graphene, and displacing the NHS ester portions with detection molecules having an accessible amine group so as to create an amide bond between the graphene layer and a detection molecule.

The present invention provides methods of functionalizing a graphene field effect transistor having a graphene layer, comprising exposing the graphene layer to Ni-nitrilotriacetic acid molecules having $Ni^{2+}$ cations so to create bonds between the nitrilotriacetic acid portion and the graphene, and exposing the $Ni^{2+}$ cations to detection molecules having an accessible histidine tag so as to create bonds between the $Ni^{2+}$ cations and the detection molecule.

The present invention provides multiplexed devices comprising a substrate having a plurality of GFET sensing devices disposed thereon, at least two of the sensing devices comprising different detection molecules.

The general description and the following detailed description are exemplary and explanatory only and are not restrictive of the invention, as defined in the appended claims. Other aspects of the present invention will be apparent to those skilled in the art in view of the detailed description of the invention as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 9 illustrates exemplary schemes for linking detection molecules to graphene.

FIG. 10A Comparative model structure of the transmembrane domain of the native human μ opioid receptor. FIG. 10B Model of the computationally designed transmembrane-only water-soluble variant (wsMUR-TM) of the human μ opioid receptor. Residues are colored by amino acid types: hydrophilic in gray (GNQSTY); hydrophobic in white (ACFILMPVW); basic in dark gray (HKR); and acidic in dark gray (DE).

FIGS. 12A-12C. FIG. 12A Sequences of the crystal structure of the mouse μ opioid receptor (PDB code 4DKL; Top) (1) and the human water-soluble variant wsMUR-TM (bottom). The murine sequence (top) corresponds to that whose structure is presented in the crystal structure of the mouse μ opioid receptor. The helical secondary structure is shown as rectangles. The gray residues in between TM5 and TM6 (MLSGSK) are absent in the crystal structure. The helical secondary structure of the wsMUR-TM model is indicated by lines under the sequence. FIG. 12B Superposition of the mouse μ opioid receptor (light gray) and the wsMUR-TM model (dark gray). FIG. 12C Rendering from the "extracellular" viewpoint of the crystal structure of mouse μ opioid receptor, where the side chain of the mutated positions in wsMUR are depicted as blue spheres. The majority of mutations (50 out of 55) are located at the exterior of the structure. Five remaining positions (see also residues in rectangular boxes in FIG. 12A) are also rendered: Y130, T120, A306, N232, and K305. None of these positions are in direct contact with the irreversible antagonist β-FNA based on the crystal structure, where β-FNA was covalently attached to K235.

FIG. 15. Molar circular dichroism (CD) derived percentage of the original helical content (determined at 222 nm) of wsMUR-TM in the absence (inner-most doted plot) and the presence (outer-most doted plot) of cholesterol in buffer solution (5 mM sodium phosphate, 0.01% SDS, pH=7.0) as functions of the temperature. The addition of cholesterol stabilized the wsMUR-TM as indicated by the rightward shift of the thermostability curve.

DETAILED DESCRIPTION OF ILLUSTRATIVE EMBODIMENTS

Figure 1:
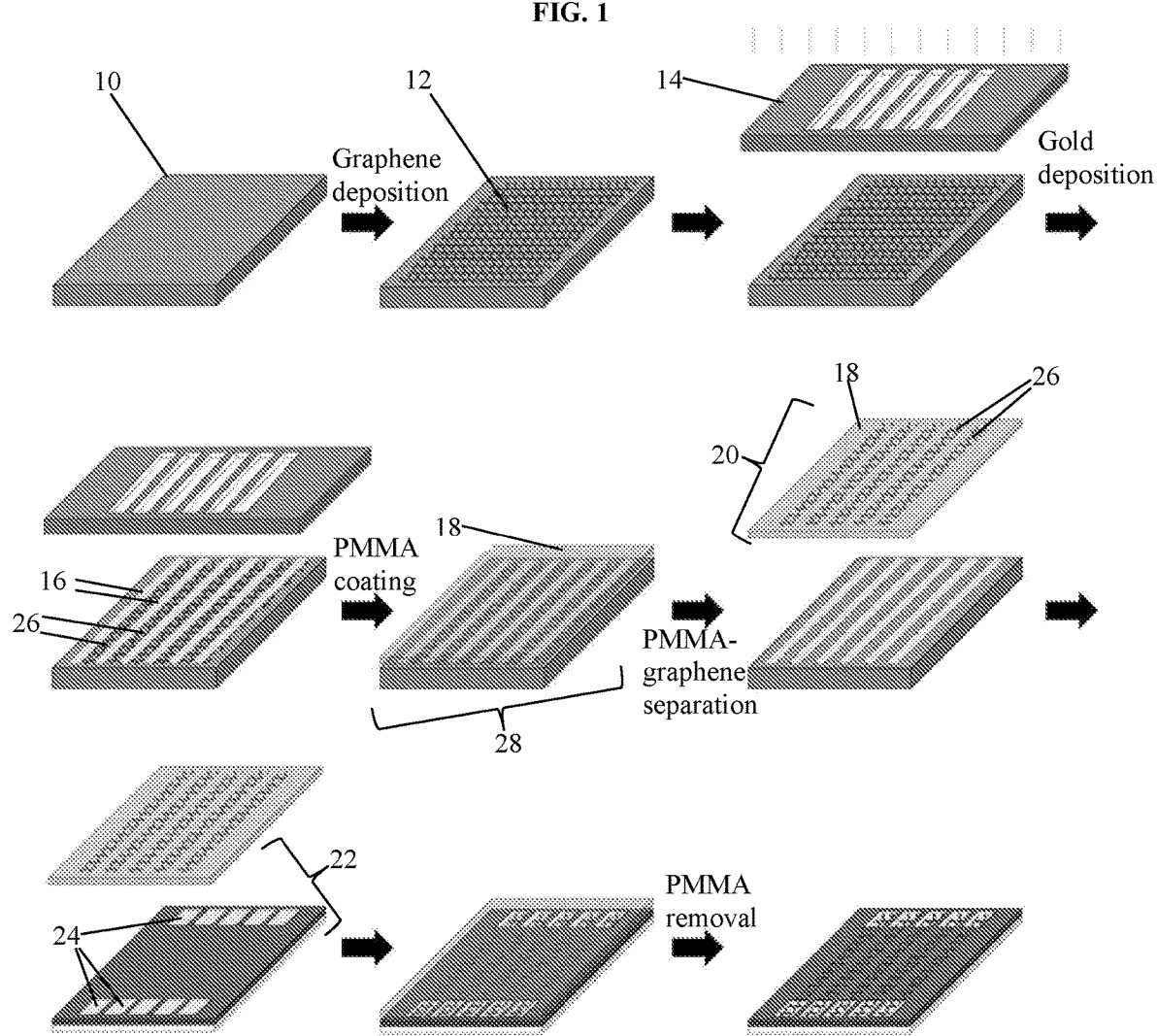
FIG. 1 illustrates an embodiment of the present invention directed to a method of graphene transistor array fabrication. Bare metal catalyst foil has graphene deposited on the foil's top surface, and then a layer of gold is patterned on the top of the graphene layer. PMMA is spun over the surface and cured. The PMMA and graphene bilayer is separated from the foil surface and transferred to a substrate having pre-fabricated electrodes.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In one aspect, the present disclosure describes methods for detecting the presence of an analyte and/or determining analyte concentration in a sample. These methods may include comprising applying a voltage to a graphene field effect transistor sensor having a conduction channel and also comprising a detection molecule being bound by an amide bond to the graphene. The methods suitably include measuring a current of the sensor, exposing the conduction channel to the sample, measuring the current of the sensor, and determining the presence and/or a concentration of analyte based upon a difference in the current. The methods suitably include determining conformational changes of the detection molecule upon analyte binding.

Also provided are methods of detecting the presence of an analyte and/or determining analyte concentration in a sample. These methods may include applying a voltage to a graphene field effect transistor sensor having a conduction channel and comprising a detection molecule being bound to the graphene, exposing the conduction channel to the sample; measuring a current of the sensor; and determining the presence, concentration, or both of the analyte based upon the current. The methods may also include determining a conformational change of the receptor related to analyte binding.

The detection molecule may be a G-protein-coupled-receptor molecule (including opioid receptors (mu, delta, or kappa), beta-adrenergic receptors, and serotonin receptors), an enzyme, a peptide, an endorphin, a receptor (for any protein-protein interactions, i.e., membrane proteins, receptors, or ion channels), a ligand (for example, morphine, methadone, fentanyl, or remifentanyl), or any combination thereof. Detection molecules may be natural (e.g., isolated from nature) or be synthetic in nature. A detection molecule can suitably be a molecule that comprises an accessible amine group, including recombinant proteins expressed with a histidine tag or an engineered cysteine residue. In some embodiments, a G-protein-coupled-receptor molecule comprising a mu-receptor protein is used as the detection molecule. In one embodiment, the mu-receptor protein can be mu-receptor protein UniProtKB: P07550 and its associated various variants with the capability to bind opioid ligand, as described herein. (Additional information may be found at www.uniprot.org.) The mu opioid receptor may be a variant engineered via mutagenesis with significant water solubility with the capability to bind opioid ligands. The analyte can be a complementary protein, small molecule, vapor phase analyte, target ligand, or any combination thereof. In some embodiments, the analyte is an opioid. These opioid analytes may include, but are not limited to, any of the opioid receptor agonists (such as morphine, methadone, fentanyl, etc.), partial agonists (such as buprenorphine, dezocine, nabulphine, etc.), and antagonists (such as naltrexone, naloxone, etc.).

Other suitable receptors and/or detection molecules are described in the "Additional Disclosure" section of this application. For example, receptors that include any of SEQ ID 1 through SEQ ID 9 are considered suitable. Receptors that include an amino acid sequence that is 90%-100% identical to any of the foregoing SEQ IDs are considered suitable; receptors that have an amino acid sequence that is at least 95% identical to SEQ ID NO: 1 are considered especially suitable.

The present disclosure also provides methods for fabricating sensing devices. These methods may include effecting deposition of a graphene layer over a top surface of a metal catalyst foil having a top surface and a bottom surface, selectively depositing a gold layer over regions of the graphene layer, spin-coating the top surface of the foil having graphene and gold layers with a layer of PMMA, baking the foil, separating the PMMA and graphene from the foil (with the gold-covered regions of graphene remaining on the foil), transferring the layer of PMMA with patterned graphene on it to a substrate having pre-fabricated electrodes such that the graphene places the prefabricated electrodes into electronic communication with one another, and removing the layer of PMMA. The metal catalyst foil may comprise ruthenium, iridium, nickel, or copper foil.

FIG. 1 depicts a method of graphene transistor array fabrication that may be used in some embodiments described herein. The graphene layer 12 can be deposited onto metal catalyst foil 10 via chemical vapor deposition (CVD), including CVD from the decomposition of methane in argon/hydrogen forming gas. Alternatively, graphene could be deposited from solution or placed on the substrate using mechanical exfoliation. The gold layer 16 can be selectively deposited using a shadow mask 14. In some embodiments of the fabrication methods, the gold layer 16 is selectively deposited in a set of strips with widths between about 20 microns and about 100 microns. The gold layer 16 may also be selectively deposited in a pattern of features having cross-sectional dimension in the range of at least about 15 micrometers. If a shadow mask is used, the regions of the foil protected by the shadow mask have exposed graphene regions 26 with no gold overlayer 16. The foil 10 can be spin-coated with a polymer, PMMA, to create a PMMA layer 18 which is treated in a manner sufficient to promote adhesion between the PMMA and the exposed graphene regions 26 but not between PMMA and the gold overlayer 16. This creates a PMMA-graphene bilayer 20 comprising PMMA layer 18 and graphene regions 26. One method of treatment is baking the foil and PMMA coating at 100° C. for two minutes. The PMMA-graphene bilayer 20 can be separated from the foil 10 via an electrochemical reaction. The entire foil sample 28 can be lowered into a solution of 0.1 M NaOH, and a voltage can be applied between the foil and the solution to create hydrogen and oxygen bubbles between the foil 10 and PMMA-graphene bilayer 20, causing separation. The separated PMMA-graphene bilayer 20 can be transferred to a substrate 22 having pre-fabricated electrodes 24 such that the graphene regions 26 place the prefabricated electrodes 24 in electronic communication with one another. In order to place the prefabricated electrodes 24 in electronic communication with one another, the substrate 22 and PMMA-graphene bilayer 20 can be baked at 150° C. for two minutes to promote adhesion between the graphene regions 26 and the substrate. The PMMA layer can be removed with acetone.

The present disclosure also provides methods for functionalizing a GFET. These methods may include exposing the GFET's graphene layer to a solution of carboxylated diazonium salt to create carboxylate groups on the graphene layer (or otherwise creating carboxylate groups or other binding sites), activating the carboxylate (or other binding) groups with a carbodiimide, stabilizing the carboxylate groups with NHS molecules, and displacing the NHS molecules with detection molecules having an accessible amine group so as to create an amide bond between the graphene layer and the receptor molecules.

Figure 3:
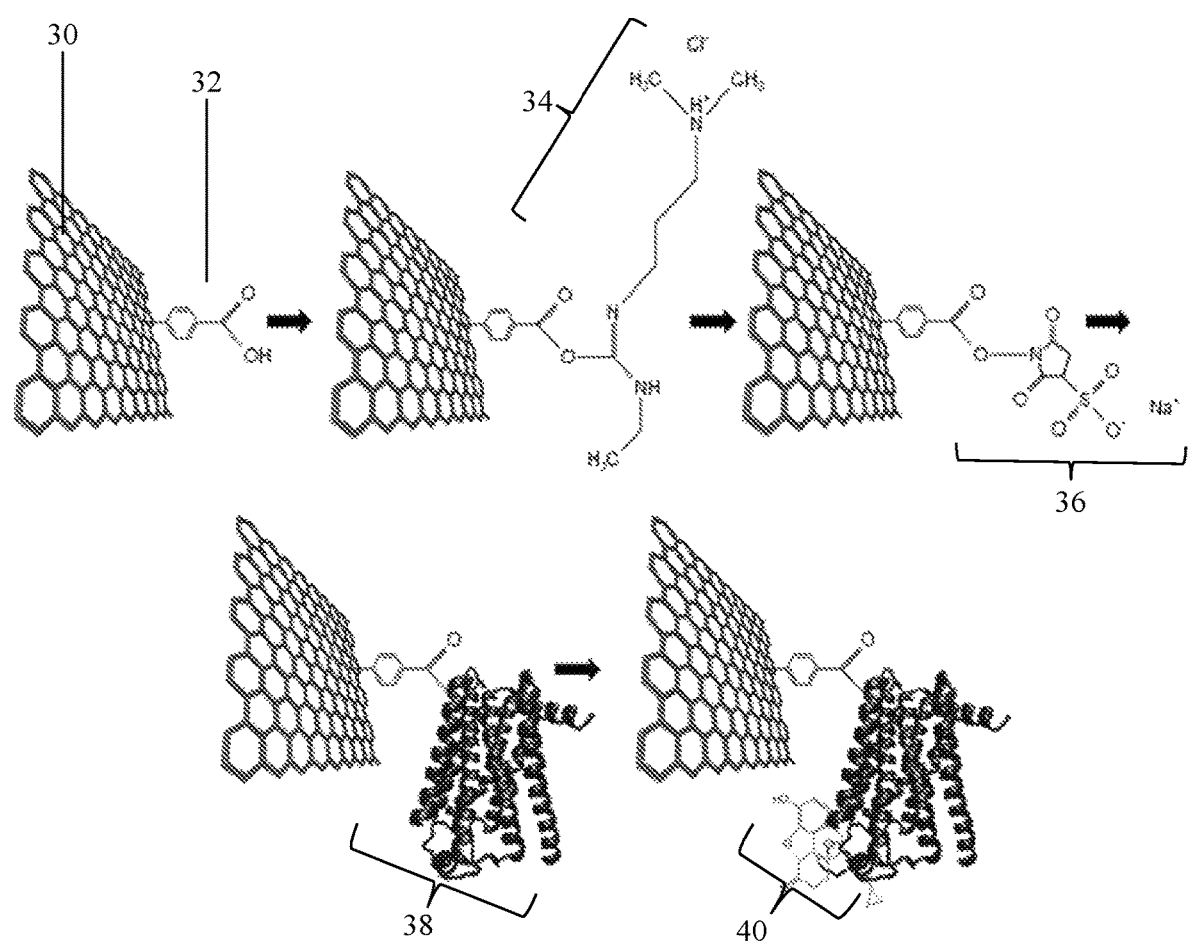
FIG. 3 shows the functionalization scheme for creating a graphene surface functionalized with an opioid receptor molecule. The figure shows a graphene layer, which is functionalized through the use of a diazonium salt. The resulting carboxylate group is then activated by EDC and stabilized with NHS. A mu-receptor protein displaces the NHS to form an amide bond. The surface can then be exposed to an opioid solution, leading to preferential binding of an opioid to the mu-receptor.

FIG. 3 shows an exemplary method of functionalizing that may be used in some embodiments described herein. A graphene layer 30 can be functionalized through the use of a diazonium salt to create a carboxylate group 32 on the surface of the graphene layer 30. The graphene layer 30 can be functionalized by incubation at 55° C. in a water solution of carboxylated diazonium salt (2.0 mg/mL in DI water). The resulting carboxylate group 32 can be activated with a carbodiimide such as 1-ethyl-3-[3-dimethylaminopropyl] carbodiimide hydrochloride (EDC) to create an unstable o-acylisourea ester intermediate 34 and stabilized with sulfo-N-hydroxysuccinimide (NHS) to create a semi-stable amine-reactive sulfo-NHS ester 36. The EDC/NHS processes can use an EDC concentration of 9 mg/15 mL MES buffer and NHS concentration of 20 mg/15 mL MES buffer. A detection molecule with an exposed amine group can displace the NHS to form a stable conjugate with a covalent amide bond. In FIG. 3, a mu-receptor protein molecule 38 is depicted displacing the NHS. In some embodiments NHS molecules can be displaced by mu-receptor proteins (3 micrograms/mL) in buffer (40 microM NaPi/260 microM NaCl/0.00004% SDS/10 microM 2-ME/pH 7.0), forming a covalent amide bond between the protein and the graphene. Such a mu-receptor protein can bind an opioid 40, as depicted in FIG. 3.

Figure 4:
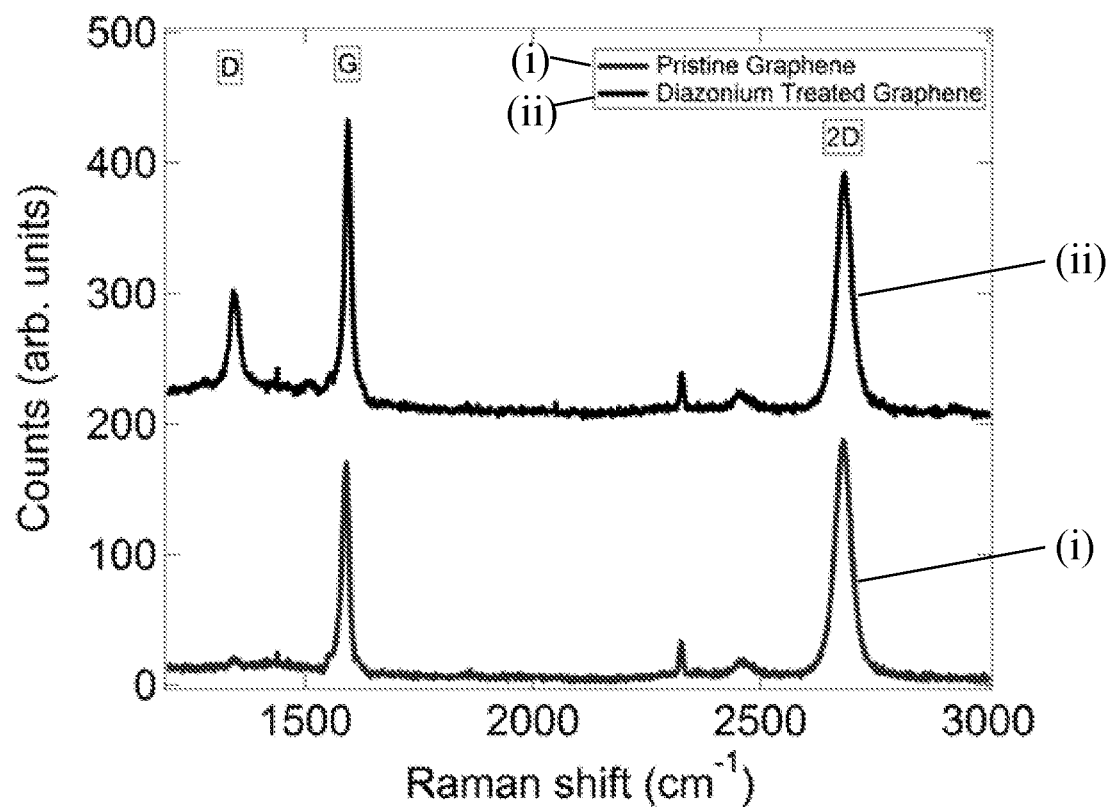
FIG. 4 shows a graphical plot of Raman spectra of a graphene surface before and after exposure to a diazonium salt. The enhanced D-band near 1360/cm after diazonium treatment indicates formation of numerous carboxy-benzene sites on the graphene surface. This is consistent with the belief that treatment creates sp3 defects in the graphene sheet, each terminated with a carboxylic group.
Figure 5A:
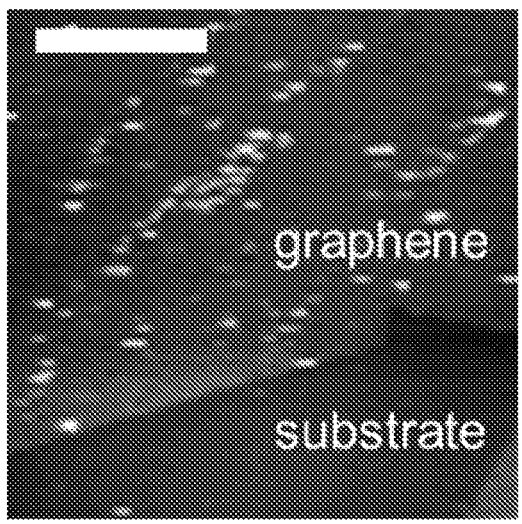
FIGS. 5A and 5B show an atomic force microscopy (AFM) image (in the image labeled FIG. 5A of the graphene and $SiO_2$ surfaces following graphene functionalization with a mu-receptor protein, and a graphical plot (in the portion labeled FIG. 5B of a histogram of the heights of AFM features. The scale bar of the AFM image is 2 microns and the image shows a factor of 10 difference in the protein attachment density between the graphene and the bare $SiO_2$ substrate. The histogram shows peaks at approximately 4 nm, 8 nm, and 12 nm, which are assigned to protein monomers and small aggregates.
Figure 5B:
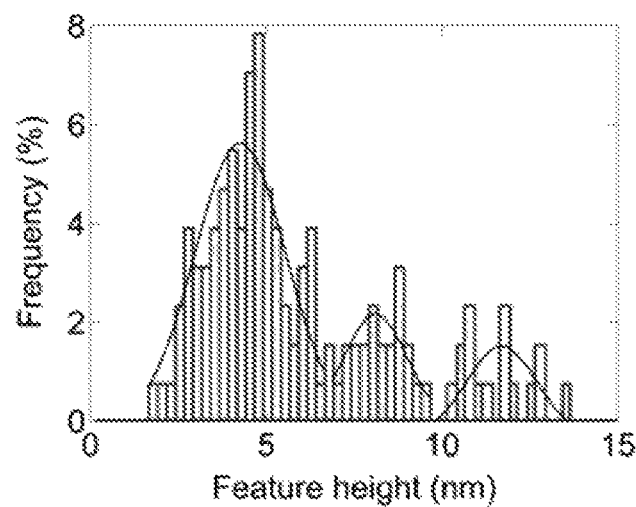

The efficacy of functionalization can be seen through the use of Raman spectroscopy, atomic force microscopy (AFM), and electronic transport measurements. FIG. 4 shows a graphical plot of a comparison of Raman spectra of pristine graphene and the same sample after incubation in the diazonium salt solution, showing a strongly increased D ("disorder") peak at ~1360/cm in the latter, consistent with the picture that this step creates sp3 defects in the graphene sheet, each terminated with a carboxylic group 32 as shown in FIG. 3. In FIG. 4, Raman spectra of graphene before, labeled as "(i)" in the plot, and after, labeled as "(ii)" in the plot, exposure to a diazonium salt solution are shown. The strongly enhanced D-band near 1360/cm after diazonium treatment indicates formation of numerous carboxy-benzene sites on the graphene surface. In FIG. 5, section "a)", an AFM image shows mu-receptor proteins (white dots) decorating the surface of graphene following functionalization of a GFET. There is a factor of about 10 difference in the protein attachment density between the graphene and the bare substrate. The scale bar is 2 microns. In FIG. 5, section "b)", histogram of the heights of AFM features shows 3 peaks around 4 nm, 8 nm, and 12 nm, assigned to protein monomers and small aggregates.

Additional information relevant to GFET functionalization is found in international patent applications PCT/US2011/042290, PCT/US2012/066064, and in U.S. patent applications 61/529,341 and 61/566,782, all of which are incorporated herein by reference in their entireties for any and all purposes.

The present disclosure also provides methods for fabricating sensing devices comprising disposing a graphene portion on an insulating substrate, the disposing being performed such that the graphene portion places two electrodes into electronic communication with one another, and linking a detection molecule to the graphene portion.

The linking may comprise formation of any or a combination of any of a variety of bonds, such as, e.g., an amide bond between the detection molecule and graphene, an imine bond between the detection molecule and graphene, a thiourea bond between the detection molecule and graphene, an aminoalcohol bond between the detection molecule and graphene, and an amide bond between the detection molecule and an intermediate molecule which is bound to the graphene through a pi-pi stacking interaction. Other covalent and ionic bonds are also suitable. Certain exemplary linkages and chemistries are shown in FIG. 9.

The graphene portion may be formed on the insulating substrate or on a first substrate. The graphene portion may be formed by removing the graphene portion from a larger graphene body. The graphene portion may be formed on a first substrate and then transferred to the insulating substrate. The graphene portion may be formed on a first substrate and then that first substrate may later be removed. The graphene portions may comprise a cross-sectional dimension in the range of at least about 15 microns. Alternatively, the graphene portions may also be formed using conventional lithographic techniques, provided that care was taken to ensure that the graphene surface was largely free of photoresist residue or other contaminants prior to linking the detection molecule to the graphene using the methods described herein.

The present disclosure also provides sensing devices that comprise a graphene portion placing first and second electrodes into electronic communication with one another, the graphene portion comprising a detection molecule bounded thereto, the detection molecule being in electronic communication with the graphene, the detection molecule being capable of complementary binding to at least one target. The device may be configured such that the device, during operation, is capable of detecting a change in signal (an electronic characteristic such as conductivity, resistance, current, or voltage) related to the complementary binding between the detection molecule and at least one target. In this way, when a target binds to the detection molecule that is in electronic communication with the graphene, an associated change in an electronic characteristic of the device is detected.

As one example, a device according to the present disclosure that includes an antibody complementary to an antigen X may be contacted with a sample that may or may not contain antigen X. If antigen X is present, antigen X will bind to the antibody. The binding will in turn change an electronic characteristic of the device, which will then be registered by the device. If antigen X is not present in the sample, the electronic characteristics of the device will remain substantially constant, and the user will understand that the analyte is not present. A voltage source can be configured to apply a voltage across the first and second electrodes.

The present disclosure also provides methods for detecting ligand binding to a functionalized graphene layer through the use of Raman spectrum. In some methods, the methods may include measuring a first G peak position in a Raman spectrum of the graphene layer, exposing the functionalized graphene layer to a sample containing ligands, and measuring a second G peak position in a Raman spectrum of the graphene layer. In other methods, the methods may include measuring a first 2D peak position in a Raman spectrum of the graphene layer, exposing the functionalized graphene layer to a sample containing ligands, and measuring a second 2D peak position in a Raman spectrum of the graphene layer.

The present disclosure also provides methods for determining analyte concentration in a sample. Such methods may include applying a voltage to a graphene field effect transistor sensor having a conduction channel and comprising a detection molecule being bound by an amide bond to the graphene, measuring a first G peak, a first 2D peak, or both, of a Raman spectrum of the graphene, exposing the conduction channel to the sample, measuring a second G peak, a second 2D peak, or both, of a Raman spectrum of the graphene, and determining a concentration of analyte based upon a difference between the first G peak, the first 2D peak, or both, and the second G peak, the second 2D peak, or both.

The present disclosure also provides multiplexed devices. Such devices may include a substrate having a plurality of sensing devices as described herein disposed thereon with at least two of the sensing devices comprising different detection molecules. Detection molecules may differ in terms of their binding affinities for different analytes, thus allowing for the construction of devices capable of simultaneously detecting the presence of two or more analytes. The devices can also comprise different detection molecules capable of binding the same analyte, thus providing some redundancy in the multiplexed device.

Example 1

Figure 2A:
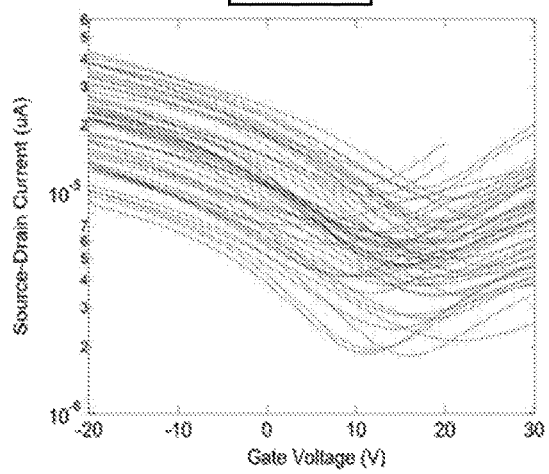
FIG. 2A shows a graphical plot of source-drain current versus back-gate voltage for a representative sample of 50 GFETs of an array of 212 devices fabricated on a single substrate. The plot shows the uniformity of the electrical characteristics of the GFETs.
Figure 2B:
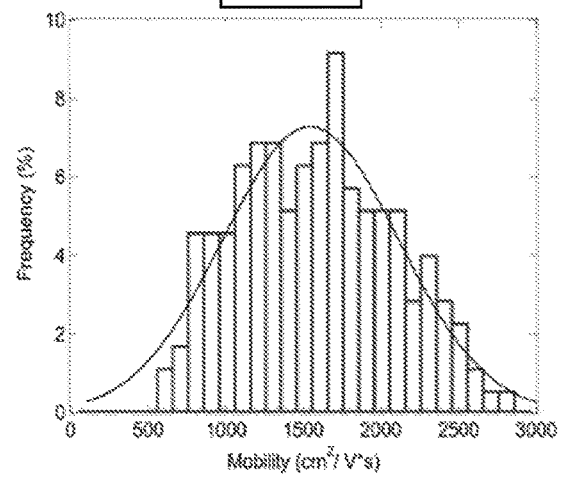
FIG. 2B shows a graphical plot of a histogram of mobility measurements for a representative sample of 50 GFETs of an array of 212 devices fabricated on a single substrate, indicating the excellent performance of these devices.
Figure 2C:
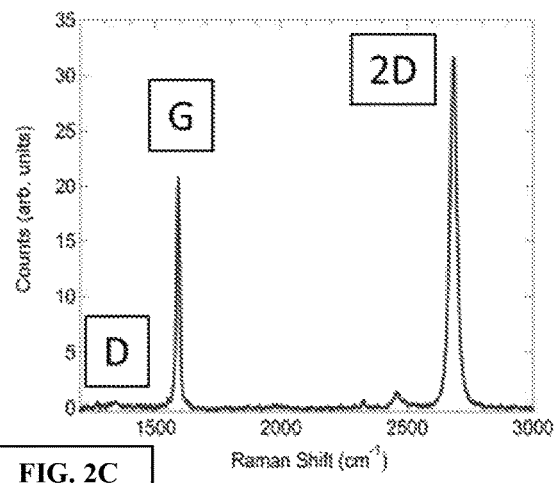
FIG. 2C shows a graphical plot of a Raman spectrum of the graphene surface of a GFET in an array of 212 devices fabricated on a single substrate. The plot shows a small D/G ratio (less than 0.03, indicating low defect density), a G/2D ratio of ~1.5, and a full width at half maximum of the 2D peak of ~30 $cm^{-1}$, all indicative of high quality monolayer graphene.
Figure 2D:
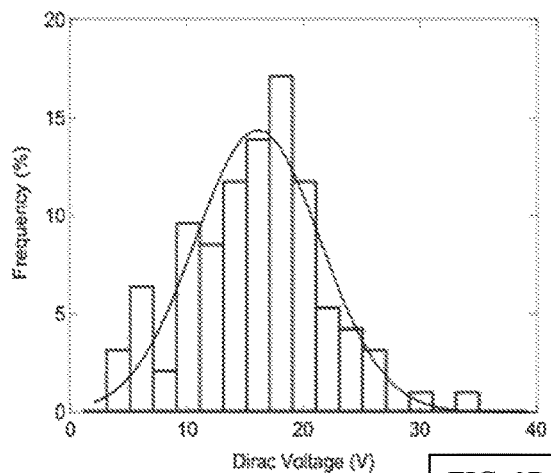
FIG. 2D shows a graphical plot of a histogram of Dirac voltage measurements for a representative sample of 50 GFETs of an array of 212 devices fabricated on a single substrate, indicating the excellent performance of these devices.
Figure 2E:
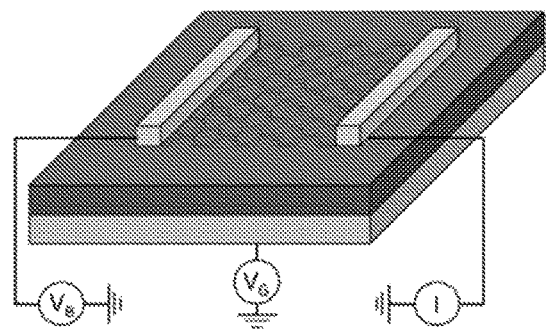
FIG. 2E is a schematic representation of a GFET device showing an insulating layer resting upon a semiconducting substrate, with graphene upon the semiconducting substrate between source and drain electrodes.

An array of 212 GFET devices was fabricated on a single substrate of about 2 cm by 2 cm dimensions, and the electrical transport properties and Raman spectra were measured. The electrical characteristics of representative devices of the array are shown in FIG. 2. A representative set of 50 I-Vg curves is displayed in the FIG. 2a), showing the uniformity of the electrical characteristics. Histograms of the mobility and Dirac voltage are depicted in FIGS. 2b) and 2d), indicating the excellent performance of these devices. The Raman spectrum in FIG. 2c) shows a small D/G ratio, a G/2D ratio of ~1.5, and a full width at half maximum of the 2D peak of ~30 cm$^{-1}$, all indicative of high quality monolayer graphene. The measured average mobility and Dirac voltage were 1500±500 cm$^2$/V-s and 15.0±5.3 V respectively. Raman spectroscopy also demonstrated the high quality of the graphene after it was incorporated into the device structure. The D/G ratio was <0.03, indicating low defect density. A yield >98% was obtained from the fabrication process.

The array of devices was fabricated using the fabrication method shown generally in FIG. 1. First, graphene was grown on copper foil by chemical vapor deposition from the decomposition of methane in argon/hydrogen forming gas. Next, a shadow mask was used to deposit gold over sections of the graphene/Cu sample in a set of strips with width of approximately 100 microns. The regions that were protected by the shadow mask had narrow graphene strips left exposed, with no gold overlayer. The whole sample was then spin-coated with a polymer, PMMA, and baked at 100° C. for 2 minutes. This treatment was sufficient to promote adhesion between the PMMA and the graphene but not between PMMA and the gold. The graphene/Cu sample was lowered into a solution of 0.1 M NaOH, where a voltage was applied between the graphene/Cu and the solution. This caused an electrochemical reaction, whereby hydrogen and oxygen bubbles were generated at the electrodes, and these bubbles formed between the copper and the graphene/PMMA causing them to separate. The PMMA scaffold had the narrow graphene strips stuck to it, and they were then transferred to a substrate with pre-fabricated electrodes. Another bake (150° C., 2 min on a hot plate) was used to promote adhesion between the graphene and the substrate and removal of the PMMA layer with acetone completed the device fabrication process.

Example 2

The GFET devices of the array fabricated in Example 1 were then functionalized with a mu receptor protein described herein to create a naltrexone binding sensor. First, the graphene was functionalized through the use of a diazonium salt. The carboxylate group was then activated by EDC and stabilized with NHS. Mu receptor protein displaced the NHS to form an amide bond. The devices were then exposed to a naltrexone solution, and naltrexone bound preferentially to the mu receptor.

The graphene transistor was functionalized by incubation at 55° C. in a water solution of carboxylated diazonium salt (2.0 mg/mL in DI water). Carboxylic acid groups from the diazonium functionalization were activated and stabilized with 1-ethyl-3-[3-dimethylaminopropyl]carbodiimide hydrochloride/sulfo-Nhydroxysuccinimide (EDC/NHS) at an EDC concentration of 9 mg/15 mL MES buffer and NHS concentration of 20 mg/15 mL MES buffer. NHS molecules were displaced by Mu receptor proteins (3 micrograms/mL) in buffer (40 microM NaPi/260 microM NaCl/0.00004% SDS/10 microM 2-ME/pH 7.0), forming a covalent amide bond between the protein and the graphene. The devices were then electrically characterized and then their sensitivity to opioid exposure was measured.

The efficacy of the functionalization procedure was demonstrated through the use of Raman spectroscopy, Atomic Force Microscopy, and electronic transport measurements.

A comparison of Raman spectra (as depicted in FIG. 4) of pristine graphene (labeled "(i)") and the same sample after incubation in the diazonium salt solution (labeled "(ii)") showed a strongly increased D ("disorder") peak at ~1360/cm in the latter, consistent with the picture that this step creates sp3 defects in the graphene sheet, each terminated with a carboxylic group (as depicted in FIG. 3).

Preferential protein attachment to the graphene surface compared to the SiO2 surface is shown in FIG. 5. A factor of about 10 difference in the protein attachment density between the graphene and the bare substrate is visible in section a) of FIG. 5. The histogram in section b) of FIG. 5 depicts the heights of AFM features shows 3 peaks ca. 4 nm, 8 nm, and 12 nm, assigned to protein monomers and small aggregates.

Figure 6:
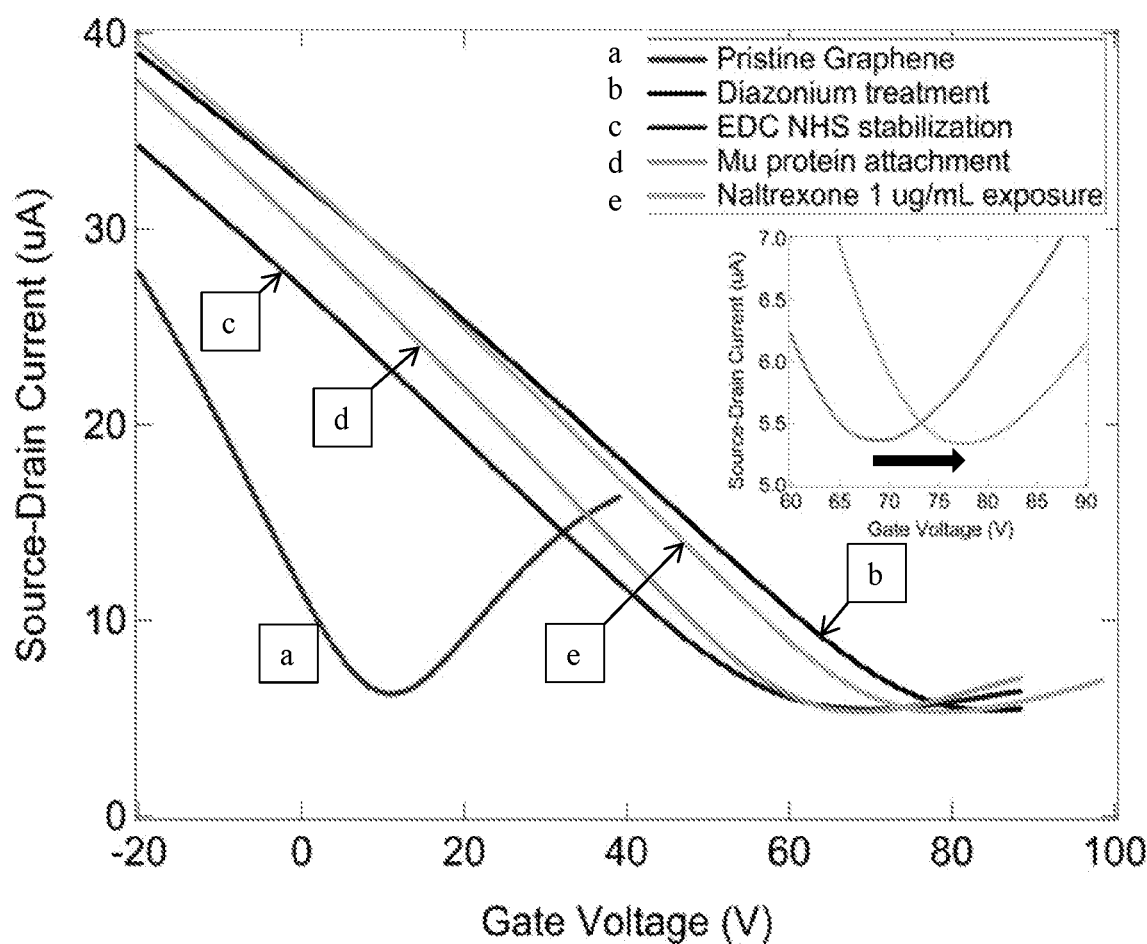
FIG. 6 shows graphical plots of source-drain current versus back gate voltage in forward gate sweep after successive functionalization steps in the fabrication of a mu-receptor protein functionalized GFET. The plot also shows current versus voltage of the functionalized GFET following exposure to a solution of 1 micrograms/mL Naltrexone in buffer. The inset shows a magnified view of a portion of the plot, which shows the shift in Dirac voltage between the functionalized GFET before and after exposure to the Naltrexone solution.

The mu protein-functionalized devices were exposed to naltrexone and showed an increase in the Dirac point voltage, i.e., the gate voltage value at which conductance is at a minimum, as a function of naltrexone concentration, as evidenced by the electrical data shown in FIG. 6. The source-drain current value is at a minimum at the gate voltage value at which conductance is at a minimum. The increase in Dirac voltage was defined as the sensing response (change in signal, i.e. electronic characteristic) for this ligand. FIG. 6 shows I-Vg plots in forward gate sweep after successive functionalization steps, labeled as curves 'a' through 'e'. The Dirac point increases following exposure to a solution of 1 micrograms/mL Naltrexone in buffer (curve 'd' to curve 'e'). The inset is a magnified view of this shift in the Dirac voltage.

Figure 7:
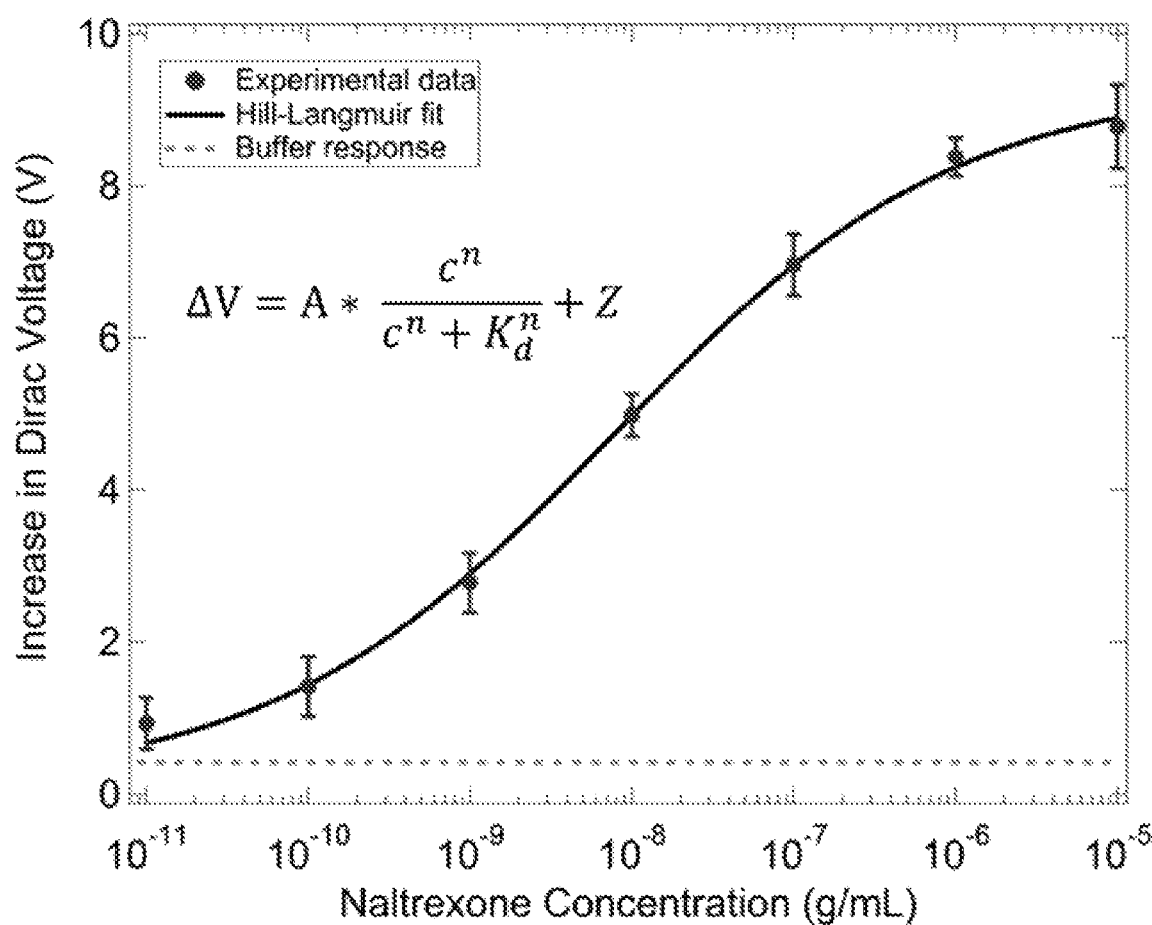
FIG. 7 shows a graphical plot of experimental data (Dirac voltage versus Naltrexone concentration) and a Hill-Langmuir fit-line for sensor responses of functionalized GFETs to Naltrexone in phosphate buffer at concentrations in the range of 10 pg/mL to 10 micrograms/mL. Each concentration was tested against 15-30 devices. The plot shows excellent agreement with the Hill-Langmuir theory of ligand-receptor binding, with a binding affinity of approximately 7.7 ng/mL. The experimental data fit to the Hill-Langmuir equation was modified with an offset (Z) to account for the small sensor response to buffer alone (shown in the plot as a dashed line) and an overall scale factor (A).

The sensor response of the devices to Naltrexone in phosphate buffer at concentrations in the range 10 pg/mL to 10 micrograms/mL was measured. Each concentration was tested against 15-30 devices. The plot of data shows excellent agreement with the Langmuir-Hill theory of ligand-receptor binding, with a binding affinity of approximately 7.7 ng/mL. FIG. 7 shows the experimental data fit to the Hill equation, modified with an offset to account for the small sensor response to buffer alone and an overall scale factor. The relevant parameters in the Hill equation are the maximum response amplitude, $A=9.3\pm0.2$ V, the binding affinity $K_d=7.7\pm1.5$ ng/mL, the cooperativity parameter $n=0.41\pm0.03$, and the offset response of the device to pure buffer $Z=0.11\pm0.04$ V. The detection limit for these devices was determined to be approximately 10 pg/mL, a factor of ~1000 smaller than the measured receptor affinity of 7.7 ng/mL.

The mu receptor was engineered to be soluble in an aqueous environment while maintaining its natural affinity for binding opioids and specificity against other compounds. Several negative control tests were performed of the device specificity, with each test conducted on 15-25 devices, and in each case the measured response was statistically consistent with zero: i) response to pure buffer ($0.03\pm0.4$ V); ii) response to 10 micrograms/mL of the GABA receptor antagonist Flumazenil ($-0.2\pm0.4$ V); iii) response to naltrexone at 10 micrograms/mL of devices prepared as described except that the exposure to modified mu receptor was omitted ($-0.3\pm0.3$ V); iv) response of an identically prepared device functionalized with anti-HER2 scFv, which was not expected to bind naltrexone ($-0.3\pm0.5$ V). The measured response to naltrexone was highly specific and believed to be due to binding of naltrexone to the engineered mu receptor rather than other locations on the surface of the functionalized graphene. The mechanism for this sensing response was presumed to be local electrostatic gating caused by a conformational change in the mu receptor protein upon binding its opioid target.

Example 3

Raman spectroscopy of the graphene layer in a functionalized GFET was used as an optical readout method to detect ligand binding. Tests were conducted ton 7-10 mu-receptor-protein-functionalized GFET devices constructed as described in Example 2, on three naltrexone concentrations. Naltrexone binding was detected through an analysis of the shift of the G peak and the 2D peak in the Raman spectrum. Table 1 and Table 2 show the results.

TABLE 1

| naltrexone concentration | Average G peak position after protein | Average G peak position after analyte | Average G peak shift | st error |
|---|---|---|---|---|
| 0 (buffer control) | 1592.06 ± 0.14 | 1592.17 ± 0.23 | 0.11 | 0.27 |
| 10 ng/mL | 1590.45 ± 0.20 | 1591.61 ± 0.13 | 1.16 | 0.24 |
| 10 micrograms/mL | 1592.86 ± 0.14 | 1594.39 ± 0.15 | 1.53 | 0.21 |

TABLE 2

| naltrexone concentration | Average 2D peak position after protein | Average 2D peak position after analyte | Average 2D peak shift | st error |
|---|---|---|---|---|
| 0 (buffer control) | 2683.96 ± 0.27 | 2684.38 ± 0.33 | 0.42 | 0.43 |
| 10 ng/mL | 2682.10 ± 0.19 | 2683.19 ± 0.20 | 1.09 | 0.28 |
| 10 micrograms/mL | 2683.86 ± 0.22 | 2685.83 ± 0.26 | 1.97 | 0.34 |

Figure 8A:
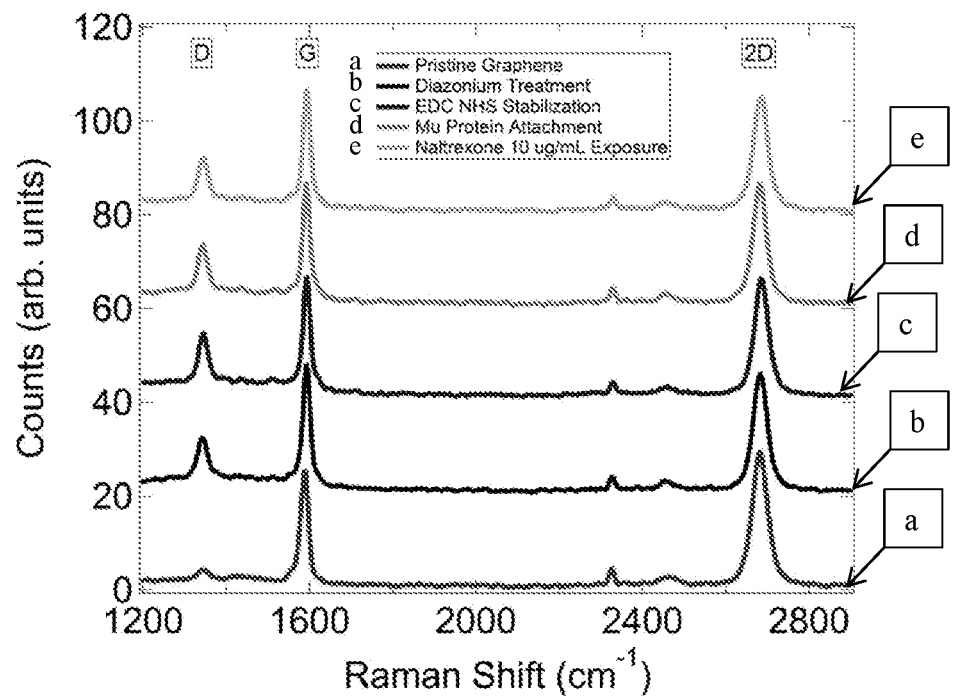
FIG. 8A shows a graphical plot of Raman spectra for functionalized graphene samples after the steps leading to protein attachment and after exposure to a solution of 10 micrograms/mL Naltrexone in buffer. The naltrexone detection "signal" is a shift in the location of the G peak and 2D peak (barely visible at this resolution).
Figure 8B:
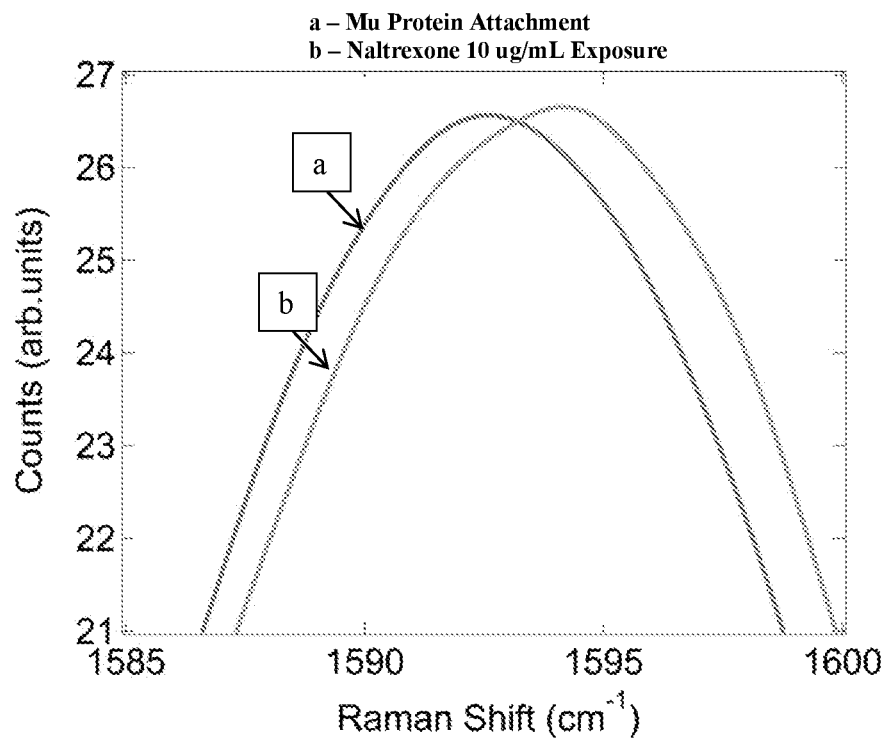
FIG. 8B shows a graphical plot of the G-peak region of the FIG. 8a Raman spectra for graphene functionalized with a mu-receptor protein before and after exposure to a solution of 10 micrograms/mL naltrexone in buffer. The Raman shift is larger due to naltrexone binding.
Figure 8C:
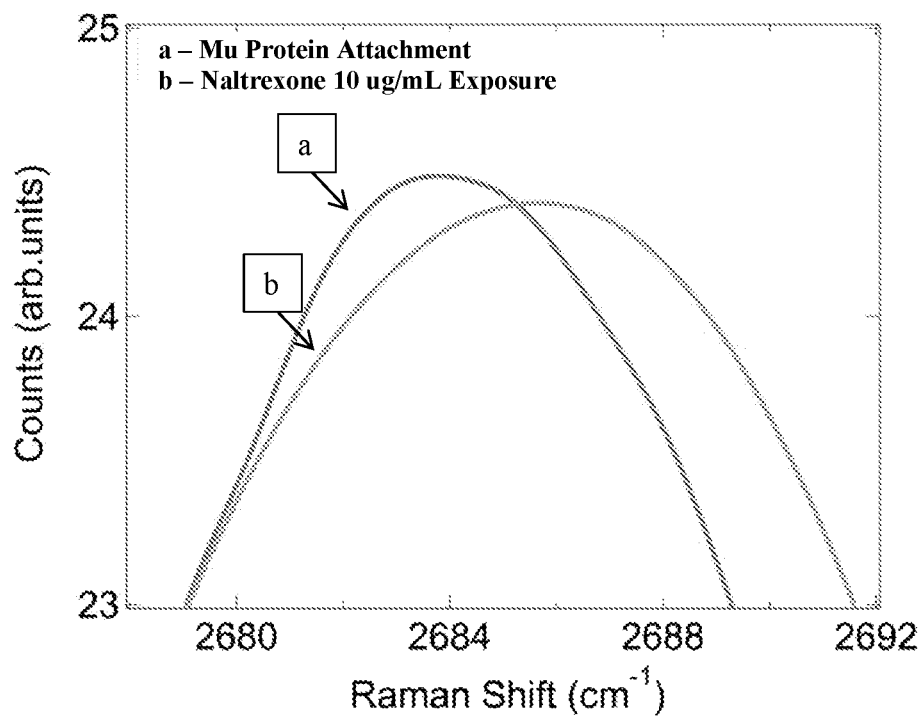
FIG. 8C shows a graphical plot of the 2D-peak region of the FIG. 8a Raman spectra for graphene functionalized with a mu-receptor protein before and after exposure to a solution of 10 micrograms/mL naltrexone in buffer. The Raman shift is larger due to naltrexone binding.
Figure 8D:
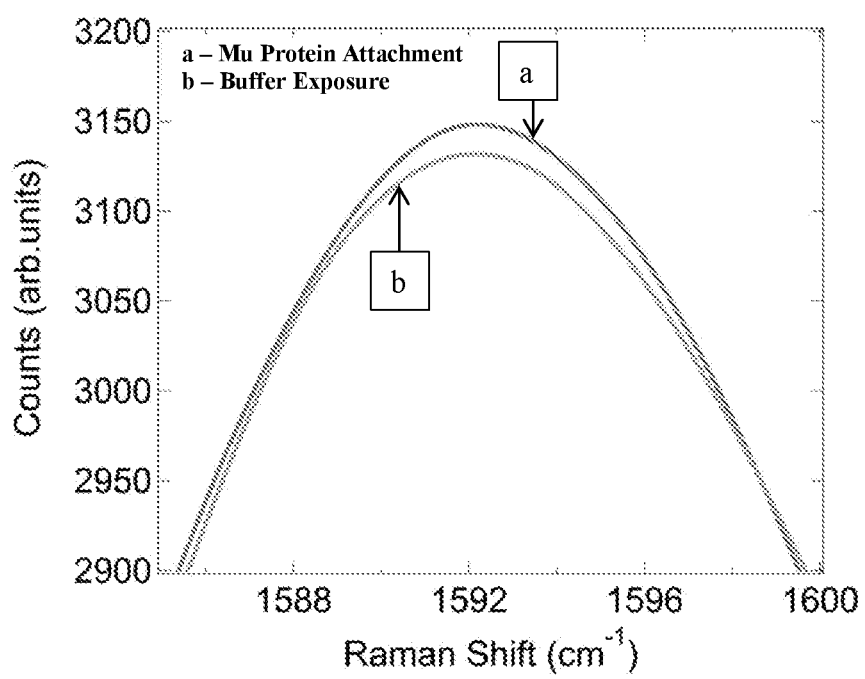
FIG. 8D shows a graphical plot of the G-peak region of the FIG. 8a Raman spectra for graphene functionalized with a mu-receptor protein before and after exposure to a solution of pure buffer. There is no observable shift in the G-peak of the Raman shift.
Figure 8E:
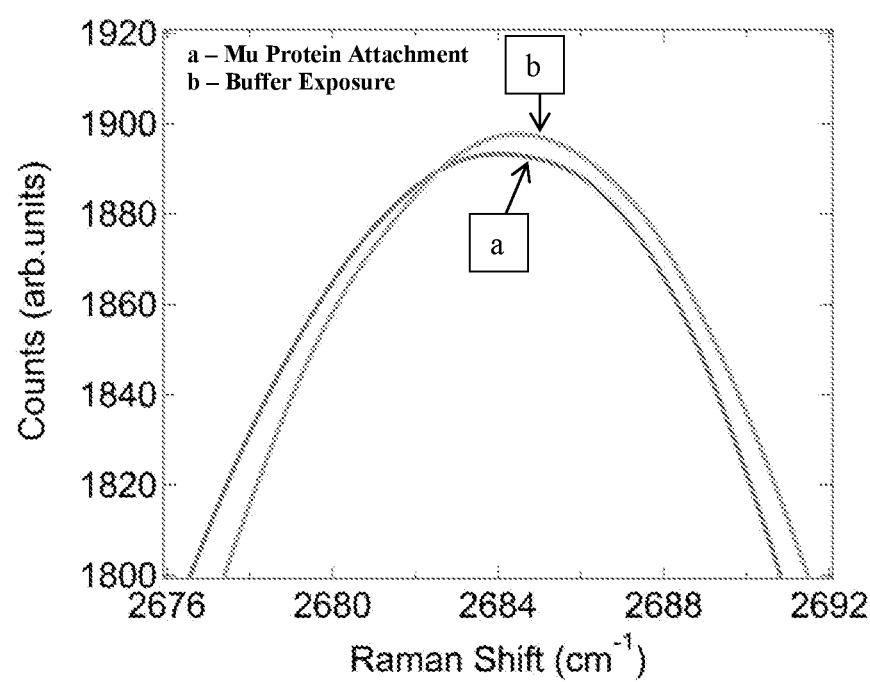
FIG. 8E shows a graphical plot of the 2D-peak region of the FIG. 8a Raman spectra for graphene functionalized with a mu-receptor protein before and after exposure to a solution of pure buffer. There is no observable shift in the 2D-peak of the Raman shift.

Statistically significant shifts in the location of the G peak and the 2D peak were observed for naltrexone concentrations of 10 ng/mL and 10 micrograms/mL, but not for pure buffer. FIGS. 8a through 8e show Raman spectra for functionalized graphene samples after the steps leading to protein attachment and after exposure to a solution of 10 micrograms/mL naltrexone in buffer. The naltrexone detection signal is a shift in the location of the G peak and 2D peak that is barely visible at the resolution of FIG. 8a. FIG. 8b depicts a "zoom in" on the G-peak region and shows the clear shift to larger Raman shift induced by naltrexone binding. A similar shift is seen in the 2D peak in FIG. 8c. No shifts were seen after exposure to pure buffer as a negative control, in FIGS. 8d and 8e.

Additional Disclosure

The G-protein-coupled receptor (GPCR) family of proteins have important roles in signal transduction and cellular response to extracellular stimuli. For this reason GPCRs are the target of many pharmaceuticals. The μ opioid receptor (MUR) is a GPCR that is the dominant target of opioids, many of which are potent analgesics widely used for the treatment of severe and chronic pain, e.g., morphine. Opioid use has soared in recent years and human MUR has been linked to abuse and many notorious side effects, including addiction and deadly respiratory depression.

The molecular mechanisms governing GPCR function remains obscure despite the profound insights obtained recently from multiple high-resolution crystal structures. Drug development and the study of the molecular mechanisms of GPCRs are impeded by limited solubility and difficulty in isolating sufficient quantities of functional receptors. These difficulties are caused in part by the large numbers of hydrophobic residues on the transmembrane, lipid-contacting protein exterior. Functional studies of MUR, and other GPCRs, could be carried out or greatly accelerated if forms of the protein existed that are water soluble, retain properties of native protein functionality, and are easily obtained in large quantity.

Described herein are recombinant integral membrane proteins having multiple transmembrane domains computationally redesigned to increase their water solubility while retaining functionally related properties. The design involves several key steps: Comparative modeling using sequence alignment and known GPCR structures (the subsequently solved structure of murine MUR provided a means to assess the quality of the comparative model); Identification and computational redesign of transmembrane exterior residues; Overexpression in E. coli and purification; Characterization of structural and ligand-binding properties in aqueous buffer. The designed water-soluble human MUR has structurally and functionally related properties comparable to the native membrane-soluble human MUR.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to ±10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about."

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

"Isolated" means altered "by the hand of man" from the natural state. If a molecule or composition occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated" as the term is employed herein.

"Polynucleotide," synonymously referred to as "nucleic acid molecule" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

A "vector" is a replicon, such as plasmid, phage, cosmid, or virus in which another nucleic acid segment may be operably inserted so as to bring about the replication or expression of the segment.

A cell has been "transformed" when exogenous or heterologous nucleic acids such as DNA have been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell, or "stable cell" is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations. In some examples provided herein, cells are transformed by transfecting the cells with DNA.

The embodiments described herein are not limited to particular methods, reagents, compounds, compositions or biological systems, which can, of course, vary. Furthermore, the terminology used herein is for the purpose of describing particular antibodies or antigen-binding fragments only, and is not intended to be limiting.

Described herein are recombinant integral membrane proteins having multiple transmembrane domains that have been engineered to be less hydrophobic, through alteration of the amino acid sequence of the native protein, but retain the ability to bind their natural ligand. The decreased hydrophobicity of the described proteins makes them more water soluble than the native protein, which allows the described proteins to be expressed in bacteria in large quantities, and isolated in the absence of membranes, all while retaining the ability to interact with known ligands in the manner of the corresponding membrane protein.

In some embodiments the described recombinant integral membrane proteins have seven transmembrane domains, with 4 of these transmembrane domains each having at least 3 amino acid mutations that decrease the overall hydrophobicity of the recombinant integral membrane protein relative to the native protein. In another embodiment, the described recombinant integral membrane proteins having seven transmembrane domains, with at least 5 of these transmembrane domains each having at least 3 amino acid mutations that decrease the overall hydrophobicity of the recombinant integral membrane protein relative to the native protein. In some embodiments, the described recombinant integral membrane proteins are variants of a native protein characterized as a G-protein-coupled receptor. For example, in some embodiments the described protein may be a recombinant form of a human mu opioid receptor. In another embodiment the described protein may be a recombinant form of a human $\beta_2$ adrenergic receptor.

In one embodiment, the described recombinant integral membrane protein has an amino acid sequence that is about 95% identical to that of SEQ ID NO: 1. In one embodiment, the described recombinant integral membrane protein has an amino acid sequence that is about 96% identical to that of SEQ ID NO: 1. In one embodiment, the described recombinant integral membrane protein has an amino acid sequence that is about 97% identical to that of SEQ ID NO: 1. In one embodiment, the described recombinant integral membrane protein has an amino acid sequence that is about 98% identical to that of SEQ ID NO: 1. In one embodiment, the described recombinant integral membrane protein has an amino acid sequence that is about 99% identical to that of SEQ ID NO: 1. In one embodiment, the described recombinant integral membrane protein has the amino acid sequence of SEQ ID NO: 1.

In one embodiment, the described recombinant integral membrane protein has an amino acid sequence that is about 95% identical to that of SEQ ID NO: 2. In one embodiment, the described recombinant integral membrane protein has an amino acid sequence that is about 96% identical to that of SEQ ID NO: 2. In one embodiment, the described recombinant integral membrane protein has an amino acid sequence that is about 97% identical to that of SEQ ID NO: 2. In one embodiment, the described recombinant integral membrane protein has an amino acid sequence that is about 98% identical to that of SEQ ID NO: 2. In one embodiment, the described recombinant integral membrane protein has an amino acid sequence that is about 99% identical to that of SEQ ID NO: 2. In one embodiment, the described recombinant integral membrane protein has the amino acid sequence of SEQ ID NO: 2.

In one embodiment, the described recombinant integral membrane protein has an amino acid sequence that is about 95% identical to that of SEQ ID NO: 3. In one embodiment, the described recombinant integral membrane protein has an amino acid sequence that is about 96% identical to that of SEQ ID NO: 3. In one embodiment, the described recombinant integral membrane protein has an amino acid sequence that is about 97% identical to that of SEQ ID NO: 3. In one embodiment, the described recombinant integral membrane protein has an amino acid sequence that is about 98% identical to that of SEQ ID NO: 3. In one embodiment, the described recombinant integral membrane protein has an amino acid sequence that is about 99% identical to that of SEQ ID NO: 3. In one embodiment, the described recombinant integral membrane protein has the amino acid sequence of SEQ ID NO: 3.

In one embodiment, the described recombinant integral membrane protein has an amino acid sequence that is about 95% identical to that of SEQ ID NO: 4. In one embodiment, the described recombinant integral membrane protein has an amino acid sequence that is about 96% identical to that of SEQ ID NO: 4. In one embodiment, the described recombinant integral membrane protein has an amino acid sequence that is about 97% identical to that of SEQ ID NO: 4. In one embodiment, the described recombinant integral membrane protein has an amino acid sequence that is about 98% identical to that of SEQ ID NO: 4. In one embodiment, the described recombinant integral membrane protein has an amino acid sequence that is about 99% identical to that of SEQ ID NO: 4. In one embodiment, the described recombinant integral membrane protein has the amino acid sequence of SEQ ID NO: 4.

In one embodiment, the described recombinant integral membrane protein has an amino acid sequence that is about 95% identical to that of SEQ ID NO: 5. In one embodiment, the described recombinant integral membrane protein has an amino acid sequence that is about 96% identical to that of SEQ ID NO: 5. In one embodiment, the described recombinant integral membrane protein has an amino acid sequence that is about 97% identical to that of SEQ ID NO: 5. In one embodiment, the described recombinant integral membrane protein has an amino acid sequence that is about 98% identical to that of SEQ ID NO: 5. In one embodiment, the described recombinant integral membrane protein has an amino acid sequence that is about 99% identical to that of SEQ ID NO: 5. In one embodiment, the described recombinant integral membrane protein has the amino acid sequence of SEQ ID NO: 5.

In one embodiment, the described recombinant integral membrane protein has an amino acid sequence that is about 95% identical to that of SEQ ID NO: 6. In one embodiment, the described recombinant integral membrane protein has an amino acid sequence that is about 96% identical to that of SEQ ID NO: 6. In one embodiment, the described recombinant integral membrane protein has an amino acid sequence that is about 97% identical to that of SEQ ID NO: 6. In one embodiment, the described recombinant integral membrane protein has an amino acid sequence that is about 98% identical to that of SEQ ID NO: 6. In one embodiment, the described recombinant integral membrane protein has an amino acid sequence that is about 99% identical to that of SEQ ID NO: 6. In one embodiment, the described recombinant integral membrane protein has the amino acid sequence of SEQ ID NO: 6.

In one embodiment, the described recombinant integral membrane protein has an amino acid sequence that is about 95% identical to that of SEQ ID NO: 7. In one embodiment, the described recombinant integral membrane protein has an amino acid sequence that is about 96% identical to that of SEQ ID NO: 7. In one embodiment, the described recombinant integral membrane protein has an amino acid sequence that is about 97% identical to that of SEQ ID NO: 7. In one embodiment, the described recombinant integral membrane protein has an amino acid sequence that is about 98% identical to that of SEQ ID NO: 7. In one embodiment, the described recombinant integral membrane protein has an amino acid sequence that is about 99% identical to that of SEQ ID NO: 7. In one embodiment, the described recombinant integral membrane protein has the amino acid sequence of SEQ ID NO: 7.

In one embodiment, the described recombinant integral membrane protein has an amino acid sequence that is about 95% identical to that of SEQ ID NO: 8. In one embodiment, the described recombinant integral membrane protein has an amino acid sequence that is about 96% identical to that of SEQ ID NO: 8. In one embodiment, the described recombinant integral membrane protein has an amino acid sequence that is about 97% identical to that of SEQ ID NO: 8. In one embodiment, the described recombinant integral membrane protein has an amino acid sequence that is about 98% identical to that of SEQ ID NO: 8. In one embodiment, the described recombinant integral membrane protein has an amino acid sequence that is about 99% identical to that of SEQ ID NO: 8. In one embodiment, the described recombinant integral membrane protein has the amino acid sequence of SEQ ID NO: 8.

| SEQ ID NO. | Construct Name | Amino Acid Sequence (excluding signal sequence) |
|---|---|---|
| 1 | wsMur-TM | SMITAIKIHEEYKKVCEEGKKGNKLVMEVIVRYTKMK TATNIYIFNLAKADALAESTLPFQSVNKLMGTWPFGTI LCKKVISIDYYNMFTSIFTLCTMSVDRYIAVCHPVKAL DFRTPRNAKEENEKNWKLSSEIGKPVEKKATTKYRQG |

-continued

| SEQ ID NO. | Construct Name | Amino Acid Sequence (excluding signal sequence) |
|---|---|---|
| | | SIDCTLTFSHPTWYWEDKLKDEVFKKAFEEPVKKIKE<br>CYGLMILRLKSVRMLSGSKEKDRNLRRITRMVLVVVE<br>VFIKCWTEIHKYVKEGKLVTIPETTFQTVSWHECIAKG<br>YKNSCENPKLYEELDENFKRCFREFC |
| 2 | wsMUR-TM+7mut | SMITAIKILEEYKKVCEEGRKGNKLVMEVIVRYTKMK<br>TATNIYIFNLAKADALAESTLPFQSVNKLMGTWPFGTI<br>LCKKVISIDYYNMFTSIFTLCTMSVDRYIAVCHPVKAL<br>DFRTPRNAKEHNEKNWKLSSEIGKPVEKRATTKYRQG<br>SIDCTLTFSHPTWYWEDKLKDTVFKKAFEEPVKVIKE<br>CYGLMILRLKSVRMLSGSKEKDRNLRRITRMVLVVVE<br>VFIKCWTEIHKYVKEGKL |
| 3 | G-min | SEKKREKIFQEYKKVYEEGKEGNKLVVDVIERYTKM<br>KTATNDYIRNLAEADMKATETLPYQSENYLKGTWPF<br>GTEECKKVISQDYYNMFTSIETLKTMSEDRYIAVEHPV<br>KALDFRTPRDAQEKNKENWEKSKKIGEPVEKSATTKY<br>RQGSIDCTLTFSHPTWYWENKQKQKVFEEAFKKPVEE<br>IKKKHEEMQKRLKSVRMLSGSKEKDRNLRRITRMVM<br>EVVQVFIKHWDPIHKYVKDKAEKTIPETTFQTKKWHE<br>SIIEGYKNSDHNPKLYDENDENFKRHFREFK |
| 4 | H-min | SEKKKEEIWKEYKEWIEKGKKGNKLVMEVIERYTKM<br>KTATNDYIKNLAEADWKATETLPEQSKNYLEGTWPF<br>GKEKCKEVISRDYYNMFTSIYTLKTMSKDRYIAVDHP<br>VKALDFRTPREAKKENKKNWEESKKIGEPVKKDATT<br>KYRQGSIDCTLTFSHPTWYWENKQKEEVFKKAFEEPV<br>KDIEEQKKKMDERLKSVRMLSGSKEKDRNLRRITRM<br>VWEVVKKFFEKWKPIHEEVKKKAEKTIPETTFQTEEW<br>HKKIYEGYKNSEENPKLYDEKDENFKREFREFE |
| 5 | I-min | SEEKKKKIDEEYKKQIEEGKKGNKLVEDVIERYTKMK<br>TATNIYIKNLAQADQGATKTLPEQSKNYLEGTWPFGK<br>EKCKEVISKDYYNMFTSIWTLDTMSEDRYIAVEHPVK<br>ALDFRTPRKAKEENKKNWEESKKIGEPVKKEATTKYR<br>QGSIDCTLTFSHPTWYWENKWKEEVFKKAFEEPVKKI<br>EERKKKMEERLKSVRMLSGSKEKDRNLRRITRMVEN<br>VVKRFEEHWKPIHERVKEKAKKTIPETTFQTEEWHKEI<br>QKGYENSKENPKLYEKEDENFKREFREFK |
| 6 | D-min | SEETAEEIEKQYKEVIEKGKKGNKLVKEVIERYTKMK<br>TATNIYIWNLAEADLKATETLPKQSQNYLEGTWPFGQ<br>EDCKNVISIDYYNMFTSIWTLATMSEDRYIAVAHPVK<br>ALDFRTPREAEKENKKNWEESKKIGEPVKKDATTKYR<br>QGSIDCTLTFSHPTWYWENDLKDDVFKKAFEEPVKKI<br>EEAYKKMQERLKSVRMLSGSKEKDRNLRRITRMVWK<br>VVQIFIEAWDPIHKYVIEKAKETIPETTFQTEEWHKSIA<br>EGYKNSAENPELYKKDDENFKRTFREFE |
| 7 | BAD3 | MAHHHHHHVMGQPGNGSAFLLAPNGSHAPDHDVTQ<br>QRDEEWVKGQGKKMSEIVKKIVEGNKLVITAIKKFER<br>LQTVTNYFITSLAEADLKMGEAVVPYGAAHILKKMW<br>TYGNKWCEYWTSIDVLTVTASIETLDVIAEDRYKAITS<br>PFKYQSELTKNKAREEIKKVWERSGKTSFDPIQKHKY<br>RATHQEAINCYANETCCDFFTNQDYAKKSSKESFYEP<br>LKKMKEVYSRVEQEAKRQLQKIDKSEGRFHVQNLSQ<br>VEQDGRTGHGLRRSSKESLKEHKALKTLGEIMGTFTK<br>QWEPFFKVNEEHVKQDNKIRKEEYIKLNWEGYKNSG<br>ENPKIYERSPDFRIAFQELKSLRRSSLKAYGNGYSSNG<br>NTGEQSGYHVEQEKENKLLAEDLPGTEDFVGHQGTV<br>PSDNIDSPGRNASTNDSLL |
| 8 | BAD4 | MAHHHHHHVMGQPGNGSAFLLAPNGSHAPDHDVTQ<br>QRDEEWVKGTGRQMSEIVKKIVEGNKLVITAIQKFER<br>LQTVTNYFITSLAEADLKMGEAVVPYGAAHILKKMW<br>TYGNRWCEYWTSIDVLTVTASIETLDVIAEDRYKAITS<br>PFKYQSELTKNKAREEIKKVWERSGKTSFDPIQKHKY<br>RATHQEAINCYANETCCDFFTNQDYAKKSSKQSFYEP<br>LQKMKDVYSRVEQEAKRQLQKIDKSEGRFHVQNLSQ<br>VEQDGRTGHGLRRSSKESLKEHKALKTLGEIMGTFTR<br>QWDPFFKVNEEHVKQDNKIRKEEYIKLNWEGYKNSG<br>ENPKIYERSPDFRIAFQELRSLRRSSLKAYGNGYSSNG<br>NTGEQSGYHVEQEKENKLLAEDLPGTEDFVGHQGTV<br>PSDNIDSPGRNASTNDSLL |

-continued

| SEQ ID NO. | Construct Name | Amino Acid Sequence (excluding signal sequence) |
|---|---|---|
| 9 | Native MUR-TM | SMITAITIMALYSIVCVVGLFGNFLVMYVIVRYTKMKT<br>ATNIYIFNLALADALATSTLPFQSVNYLMGTWPFGTIL<br>CKIVISIDYYNMFTSIFTLCTMSVDRYIAVCHPVKALDF<br>RTPRNAKIINVCNWILSSAIGLPVMFMATTKYRQGSID<br>CTLTFSHPTWYWENLLKICVFIFAFIMPVLIITVCYGLM<br>ILRLKSVRMLSGSKEKDRNLRRITRMVLVVVAVFIVC<br>WTPIHIYVIIKALVTIPETTFQTVSWHFCIALGYTNSCL<br>NPVLYAFLDENFKRCFREFC |

In some aspects the described recombinant integral membrane proteins can be further modified to have additional sequences present such as a signal sequence or an epitope tag to allow for selective binding or purification of the protein without the need to contact structural epitopes of the variant protein. As discussed herein, the epitope tag may be a polyhistidine tag or an HA epitope tag. In some embodiments the polyhistidine tag will include at least 5 consecutive histidine amino acid residues.

Polynucleotides encoding the described nucleotide sequences are also within the scope of the subject matter described herein. A polynucleotide encoding any one of the amino acid sequences for the described recombinant integral membrane proteins is provided. In one embodiment the described polynucleotide encodes a recombinant integral membrane protein having an amino acid sequence that is about 95% identical to that of SEQ ID NO: 1. In one embodiment the described polynucleotide encodes a recombinant integral membrane protein having an amino acid sequence that is about 96% identical to that of SEQ ID NO: 1. In one embodiment the described polynucleotide encodes a recombinant integral membrane protein having an amino acid sequence that is about 97% identical to that of SEQ ID NO: 1. In one embodiment the described polynucleotide encodes a recombinant integral membrane protein having an amino acid sequence that is about 98% identical to that of SEQ ID NO: 1. In one embodiment the described polynucleotide encodes a recombinant integral membrane protein having an amino acid sequence that is about 99% identical to that of SEQ ID NO: 1. In one embodiment the described polynucleotide encodes a recombinant integral membrane protein having the amino acid sequence of SEQ ID NO: 1.

In one embodiment the described polynucleotide encodes a recombinant integral membrane protein having an amino acid sequence that is about 95% identical to that of SEQ ID NO: 2. In one embodiment the described polynucleotide encodes a recombinant integral membrane protein having an amino acid sequence that is about 96% identical to that of SEQ ID NO: 2. In one embodiment the described polynucleotide encodes a recombinant integral membrane protein having an amino acid sequence that is about 97% identical to that of SEQ ID NO: 2. In one embodiment the described polynucleotide encodes a recombinant integral membrane protein having an amino acid sequence that is about 98% identical to that of SEQ ID NO: 2. In one embodiment the described polynucleotide encodes a recombinant integral membrane protein having an amino acid sequence that is about 99% identical to that of SEQ ID NO: 2. In one embodiment the described polynucleotide encodes a recombinant integral membrane protein having the amino acid sequence of SEQ ID NO: 2.

In one embodiment the described polynucleotide encodes a recombinant integral membrane protein having an amino acid sequence that is about 95% identical to that of SEQ ID NO: 3. In one embodiment the described polynucleotide encodes a recombinant integral membrane protein having an amino acid sequence that is about 96% identical to that of SEQ ID NO: 3. In one embodiment the described polynucleotide encodes a recombinant integral membrane protein having an amino acid sequence that is about 97% identical to that of SEQ ID NO: 3. In one embodiment the described polynucleotide encodes a recombinant integral membrane protein having an amino acid sequence that is about 98% identical to that of SEQ ID NO: 3. In one embodiment the described polynucleotide encodes a recombinant integral membrane protein having an amino acid sequence that is about 99% identical to that of SEQ ID NO: 3. In one embodiment the described polynucleotide encodes a recombinant integral membrane protein having the amino acid sequence of SEQ ID NO: 3.

In one embodiment the described polynucleotide encodes a recombinant integral membrane protein having an amino acid sequence that is about 95% identical to that of SEQ ID NO: 4. In one embodiment the described polynucleotide encodes a recombinant integral membrane protein having an amino acid sequence that is about 96% identical to that of SEQ ID NO: 4. In one embodiment the described polynucleotide encodes a recombinant integral membrane protein having an amino acid sequence that is about 97% identical to that of SEQ ID NO: 4. In one embodiment the described polynucleotide encodes a recombinant integral membrane protein having an amino acid sequence that is about 98% identical to that of SEQ ID NO: 4. In one embodiment the described polynucleotide encodes a recombinant integral membrane protein having an amino acid sequence that is about 99% identical to that of SEQ ID NO: 4. In one embodiment the described polynucleotide encodes a recombinant integral membrane protein having the amino acid sequence of SEQ ID NO: 4.

In one embodiment the described polynucleotide encodes a recombinant integral membrane protein having an amino acid sequence that is about 95% identical to that of SEQ ID NO: 5. In one embodiment the described polynucleotide encodes a recombinant integral membrane protein having an amino acid sequence that is about 96% identical to that of SEQ ID NO: 5. In one embodiment the described polynucleotide encodes a recombinant integral membrane protein having an amino acid sequence that is about 97% identical to that of SEQ ID NO: 5. In one embodiment the described polynucleotide encodes a recombinant integral membrane protein having an amino acid sequence that is about 98% identical to that of SEQ ID NO: 5. In one embodiment the described polynucleotide encodes a recombinant integral membrane protein having an amino acid sequence that is about 99% identical to that of SEQ ID NO: 5. In one embodiment the described polynucleotide encodes a recombinant integral membrane protein having the amino acid sequence of SEQ ID NO: 5.

In one embodiment the described polynucleotide encodes a recombinant integral membrane protein having an amino acid sequence that is about 95% identical to that of SEQ ID NO: 6. In one embodiment the described polynucleotide encodes a recombinant integral membrane protein having an amino acid sequence that is about 96% identical to that of SEQ ID NO: 6. In one embodiment the described polynucleotide encodes a recombinant integral membrane protein having an amino acid sequence that is about 97% identical to that of SEQ ID NO: 6. In one embodiment the described polynucleotide encodes a recombinant integral membrane protein having an amino acid sequence that is about 98% identical to that of SEQ ID NO: 6. In one embodiment the described polynucleotide encodes a recombinant integral membrane protein having an amino acid sequence that is about 99% identical to that of SEQ ID NO: 6. In one embodiment the described polynucleotide encodes a recombinant integral membrane protein having the amino acid sequence of SEQ ID NO: 6.

In one embodiment the described polynucleotide encodes a recombinant integral membrane protein having an amino acid sequence that is about 95% identical to that of SEQ ID NO: 7. In one embodiment the described polynucleotide encodes a recombinant integral membrane protein having an amino acid sequence that is about 96% identical to that of SEQ ID NO: 7. In one embodiment the described polynucleotide encodes a recombinant integral membrane protein having an amino acid sequence that is about 97% identical to that of SEQ ID NO: 7. In one embodiment the described polynucleotide encodes a recombinant integral membrane protein having an amino acid sequence that is about 98% identical to that of SEQ ID NO: 7. In one embodiment the described polynucleotide encodes a recombinant integral membrane protein having an amino acid sequence that is about 99% identical to that of SEQ ID NO: 7. In one embodiment the described polynucleotide encodes a recombinant integral membrane protein having the amino acid sequence of SEQ ID NO: 7.

In one embodiment the described polynucleotide encodes a recombinant integral membrane protein having an amino acid sequence that is about 95% identical to that of SEQ ID NO: 8. In one embodiment the described polynucleotide encodes a recombinant integral membrane protein having an amino acid sequence that is about 96% identical to that of SEQ ID NO: 8. In one embodiment the described polynucleotide encodes a recombinant integral membrane protein having an amino acid sequence that is about 97% identical to that of SEQ ID NO: 8. In one embodiment the described polynucleotide encodes a recombinant integral membrane protein having an amino acid sequence that is about 98% identical to that of SEQ ID NO: 8. In one embodiment the described polynucleotide encodes a recombinant integral membrane protein having an amino acid sequence that is about 99% identical to that of SEQ ID NO: 8. In one embodiment the described polynucleotide encodes a recombinant integral membrane protein having the amino acid sequence of SEQ ID NO: 8.

In some embodiments the described polynucleotides may be a segment of a plasmid, vector, phage genome, YAC, or other gene expression system. The polynucleotides described herein may be used to transform bacteria, yeast, or mammalian cells to allow for expression of the protein that the polynucleotide encodes. Accordingly, described herein are bacteria transformed with a polynucleotide encoding any one of the recombinant integral membrane proteins described herein. In some embodiments the bacterium transformed with a polynucleotide encoding any one of the recombinant integral membrane proteins described herein may be *E. coli*.

Methods of use for the described proteins are also provided herein. In one embodiments the described recombinant integral membrane proteins may be used in a method of obtaining a recombinant, soluble integral membrane protein having seven transmembrane domains in bacteria by: expressing in bacteria a polynucleotide encoding the recombinant integral membrane protein described herein, lysing the bacteria, and collecting a recombinant, soluble integral membrane protein having seven transmembrane domains. The expressed recombinant protein may be collected from the bacterial culture supernatant, the lysed bacterial pellet, or both. Additionally, the recombinant integral membrane protein may be collected by any number of known methodologies, such as centrifugation, affinity chromatography, size exclusion chromatography, molecular weight filtration (such as dialysis or size exclusion centrifugation).

Also provided herein are methods of identifying a ligand for any one of the recombinant integral membrane proteins described herein by contacting the recombinant integral membrane protein of interest with a compound and determining whether the two have a specific interaction. In some embodiments a specific interaction between a compound and a recombinant integral membrane protein may be identified by determining a binding affinity between the two. Alternatively, the affinity of one of the recombinant integral membrane proteins described herein for a ligand could be determined by contacting the ligand with one or more such recombinant integral membrane proteins to determine the binding affinity between the two. The affinity of the interaction may be determined by any number of mechanisms, such as calorimetry, spectral absorption, time-resolved fluorescence resonance energy transfer, or surface plasmon resonance. In some embodiments, the recombinant integral membrane protein may be attached to a surface, for example by conjugation to an antibody specific for a protein tag added to the recombinant protein, to allow one or more compounds to be tested for interaction with the protein. Similar methods could also be used to assess the structural changes the described recombinant integral membrane proteins undergo upon ligand binding. For example, in one embodiment the structure of the recombinant integral membrane protein could be assessed before and after ligand binding occurs.

The following examples are provided to describe the embodiments described herein with greater detail. They are intended to illustrate, not to limit, the embodiments.

Example 4

Design of a Water-Soluble Variant of the Human MUR

Figure 10B:
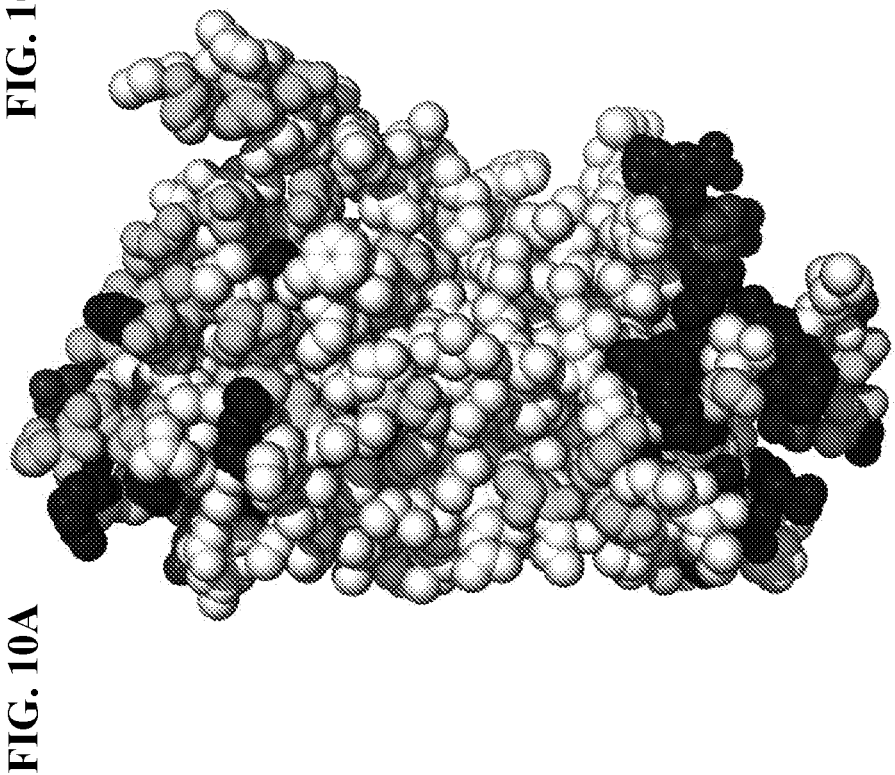
FIGS. 10A-10B. Model structure of the human μ opioid receptor transmembrane domain used during the computational design.
Figure 10A:
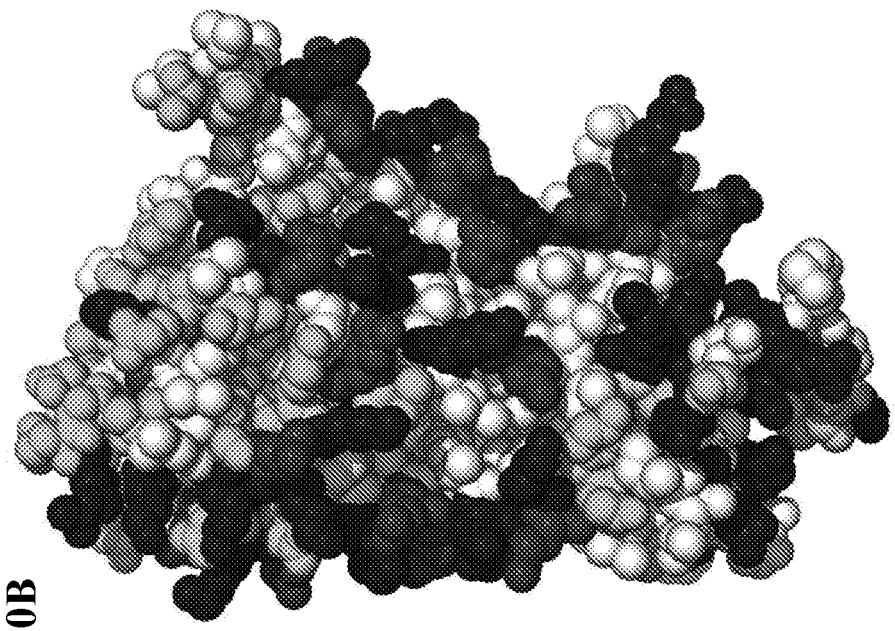
Figure 11A:
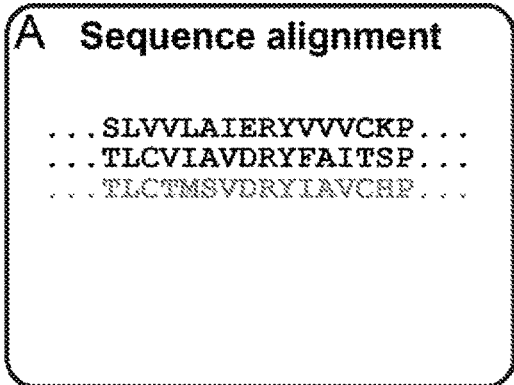
FIGS. 11A-11F. Scheme of the computational design protocol. Homology modeling: Starting from the sequence alignment between known GPCR structures (bovine rhodopsin and $\beta_2$ adrenergic receptor) and MUR FIG. 11A, 3D structures of MUR are generated FIG. 11B. Identification of exposed sites in the transmembrane portion: A representative 3D model was selected from the generated models of MUR and the transmembrane lipid-exposed positions are identified (FIG. 11C; dark gray dots). Computational design of selected exterior positions to generate a water-soluble variant: The selected exterior positions are targeted of the computational design calculation with the intention to increase the protein's solubility in water. By maximizing an effective entropy function subject to different energy constraints, the computational approach generates site-specific probability profiles, that is, the probability of each amino acid to be present at each of the targeted sites. The amino acid identities of the sites where the probability of a particular amino acid is strongly favored (equal or larger than 0.8) was chosen to be that of this most probable amino acid (FIG. 11D; light gray dots). An iterative series of such calculations were performed until the probabilities of the different positions no longer fulfill these criteria (FIG. 11E; light gray dots). At any remaining residues not yet specified with regard to amino acid identity, the most probable amino acid is selected (FIG. 11F; light gray dots).
Figure 11B:
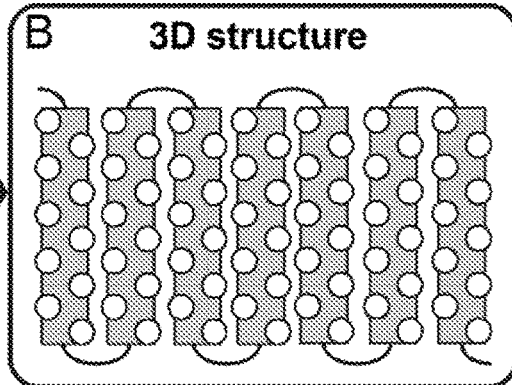
Figure 11D:
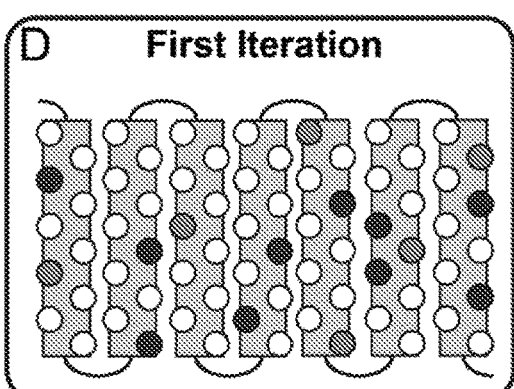
Figure 11C:
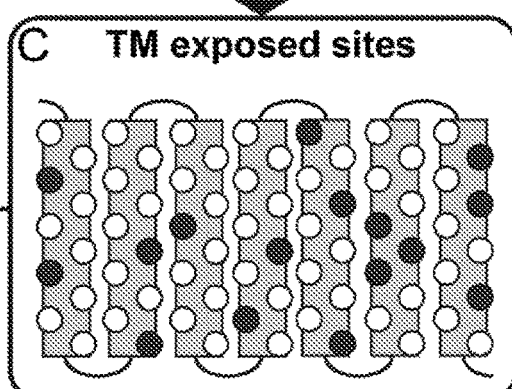
Figure 11E:
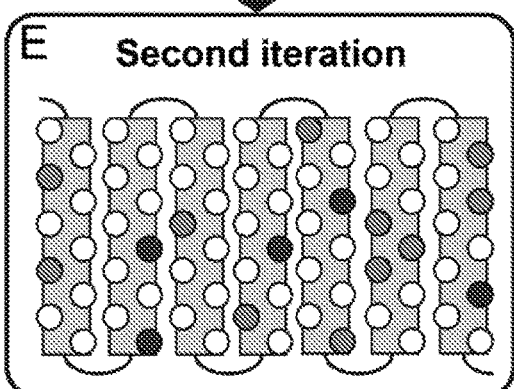
Figure 11F:
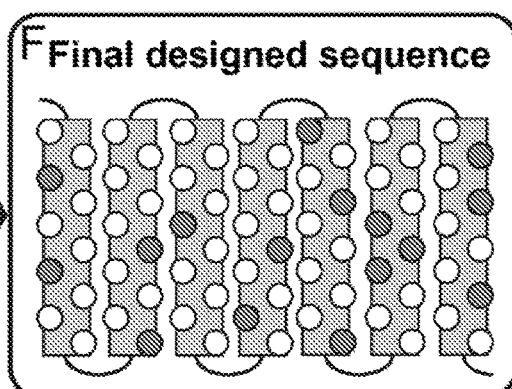

Studies were initiated to produce a comparative model of the human MUR transmembrane domain (288 residues, 66-353) using known GPCR structures (FIG. 10A). To identify the site-specific amino acid probabilities of the target positions, a statistical entropy-based formalism was used. Energy functions to quantify sequence-structure compatibility are derived from a molecular mechanics force field. To account for solvation effects and for the tendency of different amino acids to be exposed to or sequestered from water (hydrophobicity), an energy term (herein environmental energy) based on the local density of $C_\beta$ atoms of each residue and parameterized using a large database of globular proteins was used. In this case the environmental energy term was constrained to a value expected for soluble proteins of 288 residues, the size of the segment of the human MUR encompassing the TM domain. The conformational variability of the amino acid residues is addressed using a rotamer library of side chain conformations. The site-specific probabilities of the amino acids at each of the target positions are determined by maximizing an effective entropy function subject to constraints on the two energies. These probabilities were used to identify specific sequences. Residues suitable for mutation where identified as exposed, hydrophobic amino acids. Exposure is determined via inspection of model and crystallographic structures, hydrophobic scoring of the amino acids based upon empirical energy scales, and the solvent accessible area calculated for each amino acid. This resulted in identifying 55 exterior amino acids suitable for mutation. After the residues suitable for mutations were identified, the remaining residues were fixed at their wild type identities, and their side chain conformations were allowed to vary to accommodate designed mutations. All amino acids but proline and cysteine were permitted at each of the identified variable positions. A hydrophobicity scoring function (environmental energy) was applied and selected to have a value consistent with that of a globular water-soluble protein having 288 amino acids. Identification of sequence proceeded iteratively (FIG. 11). In all, 55 exterior transmembrane residues were selected for the computational redesign. A first calculation using the method described above to calculate the site-specific probabilities of the amino acids at each of 55 variable residues identified 31 positions where the probability of the selected amino acid exceeded 0.8; each such residue was mutated to this most probable amino acid, yielding the following mutations: $A75E^{1.37}$, $S78K^{1.40}$, $I79K^{1.41}$, $V83E^{1.45}$, $F89K^{1.51}$, $Y93E^{1.55}$, $T120E^{2.54}$, $K187E^{4.43}$, $I188E^{4.44}$, $V191E^{4.47}$, $C192K^{4.48}$, $A199E^{4.55}$, $L202K^{4.58}$, $M205E^{4.61}$, $N232D^{5.36}$, $L233K^{5.37}$, $I240K^{5.44}$, $F241K^{5.45}$, $I244E^{5.48}$, $M245E^{5.49}$, $L248K^{5.52}$, $V252E^{5.56}$, $A289E^{6.42}$, $V293K^{6.46}$, $P297E^{6.50}$, $I300K^{6.53}$, $I303K^{6.56}$, $I304E^{6.57}$, $A306K^{6.59}$, $L326K^{7.41}$, and $V336K^{7.51}$. The superscript notation is consistent with the Ballesteros and Weinstein indexing system: (number of the transmembrane helix).(residue number relative to most conserved residue in transmembrane helix, which is assigned position 50). These residue identities were fixed in subsequent calculations. Similarly, second and third calculations specified one ($V82E^{1.44}$) and two ($T72K^{1.34}$ and $L333E^{7.48}$), respectively, additional positions with the same probability threshold. Using the results of a fourth calculation, the most probable amino acid was selected at the remaining 21 positions, yielding a sequence and model structure for wsMUR-TM as presented in FIG. 10B. The designed sequence is presented in FIG. 12A. The recent structure of the closely related murine MUR provides an opportunity to evaluate the structure and the location of the mutated positions in wsMUR-TM. The human and mouse receptors have 94% sequence identity. The model of the human MUR and the murine crystal structure superimpose well (FIG. 12B), particularly with regard to the transmembrane helices. Only five positions in wsMUR-TM were not located in the exterior of the murine structure (T120E, Y130K, N232D, K305G, and A306K) and could in principle affect ligand binding (FIG. 12C). In the murine structure, however, these five positions residues were not among the residues that directly contact beta-Funaltrexamine (β-FNA), an irreversible antagonist of the receptor.

Other attempts to produce a water-soluble MUR protein were not successful. While some of these constructs did not express in bacteria, as was the case with the native protein, those that did express were not functional, including the native MUR protein. In all, wsMUR-TM was only one of 11 recombinant MUR constructs to have increased water solubility that could be expressed in bacteria and also bind to a native MUR ligand with comparable affinity to the native protein. Following the production of wsMUR-TM; however, several other variants were produced that could be expressed in E. coli and also retained functionality (described in Example 8).

Example 5

Expression and Purification of wsMUR-TM

A synthetic cDNA encoding the transmembrane-only water-soluble MUR variant (wsMUR-TM) was produced by DNA2.0 Inc. (Menlo Park, Calif.). The sequences were subcloned between the NdeI and XhoI restriction sites of the expression plasmid pET-28b(+) (EMD/Novagen®). E. coli BL21(DE3) cells (EMD/Novagen®) were used for expression. Cells were grown in shake flasks with Lysogeny broth medium with 30 µg/mL kanamycin to an optical density (OD) of 1.0, induced with 1 mM Isopropyl β-D-1-thiogalactopyranoside (IPTG) for 3 hours at 37° C., then pelleted by centrifugation. Cell pellets were stored at 20° C. until purification. For solubility testing, 1 OD aliquots of cells were pelleted in microcentrifuge tubes, suspended in 150 µL of TE (50 mM Tris-HCl, 1 mM EDTA, pH=8.0), then shaken with 0.3 g of glass beads (0.1 mm diameter) for 5 min. Aliquots of the resulting lysates were spun in a microcentrifuge for 1 min. Aliquots of total lysate, or the supernatant and pellet fractions after centrifugation, were analyzed on reducing sodium dodecyl sulfate (SDS) gels.

Frozen cells from 250 mL of fermentation (500-550 ODs) were thawed, and then suspended in 33.5 mL of 50 mM Tris-HCl, 1 M urea, pH=8.0. Once the pellet was fully resuspended, EDTA was added to 1 mM, Triton™ X-100 to 1%, and hen egg lysozyme to 1 µg per OD of cells, in a total volume of 37 mL. After the slurry was incubated for 20 min at room temperature (RT), MgCl2 was added to 3 mM, followed by 100 units of benzonase. The suspension was swirled, incubated another 5 min at RT, and then spun in an Oak Ridge tube at 10,000 rpm for 20 min at 20° C. in an SS-34 rotor (ravg=6.98 cm, rmax=10.70 cm).

The resulting pellet was resuspended into 35 mL of 50 mM Tris-HCl, 1 M urea, pH=8.0. Triton™ X-100 (1.5 mL of a 25% solution) and 2-mercaptoethanol (2-ME) was added to 40 mM. The tube was inverted several times, and then spun as above.

The following steps were designed to resemble those that had been used to dissolve and purify recombinant forms of native µ opioid receptor. The pellet from the above washes was resuspended into 5 mL of buffer phosphate Tris buffer (100 mM phosphate, 10 mM Tris, adjusted to pH=8.0 with NaOH) and dispersed by drawing through a pipet followed by a 25 gauge needle. The volume was then raised to 37 mL by addition of phosphate Tris buffer, and 2-ME was then added to 40 mM. The tube was inverted to mix, then spun as above.

The resulting pellet was dispersed into 36 mL of PT as described above. The suspension was then mixed with an equal volume of phosphate Tris buffer containing 0.2% SDS and 10 mM 2-ME. The suspension was rocked until it became almost clear (60-90 min) The suspension was then poured into two 38 mL Oak Ridge tubes. These were spun tube at 12,000 rpm for 20 minutes at 20° C. in an SS-34 rotor.

Since an initial exposure to 0.1% SDS was required during purification, the purified wsMUR-TM in solution may still contain small amounts of SDS due to the difficulty of removing SDS from proteins. In order to avoid protein aggregation, 0.01% of SDS was utilized in the final buffer solutions for functional assays. Using binding and crystallographic studies, it has been shown that such small amounts of SDS do not disrupt the tertiary structure and/or the ligand binding capabilities of some proteins. Conversely, a much higher concentration of SDS (0.1%) and other anionic detergents are required for the "solubilization" of the native human MUR.

Figure 13:
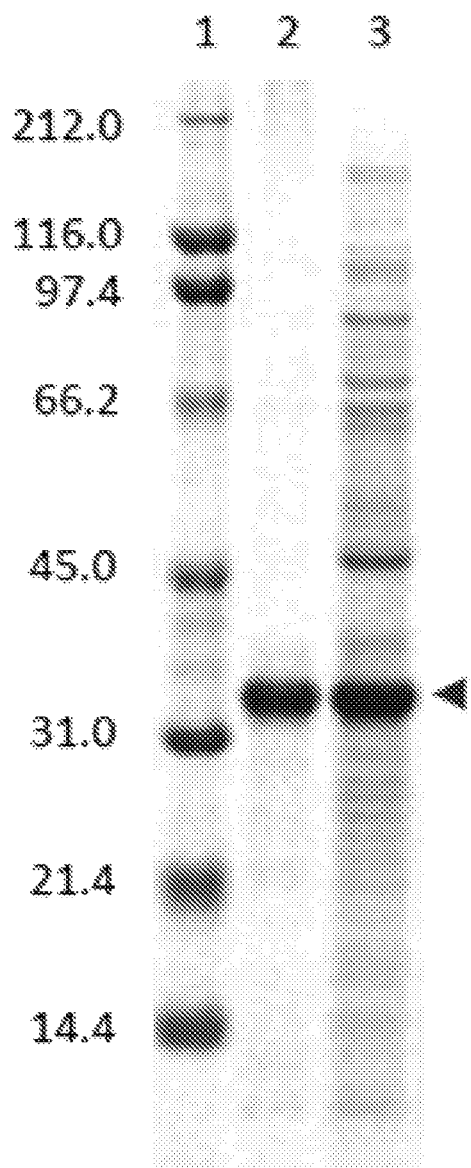
FIG. 13. Overexpression and verification of wsMUR-TM. A SDS-PAGE gel for wsMUR-TM is shown where lane 1 correspond to the molecular weight standard, lane 2 to purified wsMUR-TM and lane 3 to expressed wsMUR-TM in the crude material. The band corresponding to the wsMUR-TM appears at approximately 36 kDa.

Attempts to express the native full-length human MUR in E. coli were unsuccessful presumably due to the protein's toxicity. In contrast, wsMUR-TM expressed well and was isolated with high purity using affinity chromatography (FIG. 13). The yield was ~20 mg/L of shake flask culture. An initial exposure to ~0.1% sodium dodecyl sulfate (SDS) was required to purify the receptors. After dialysis to remove non-bound SDS, the purified variant were soluble at 6 mg/mL in buffer solution (130 mM NaCl, 20 mM NaHPO4, pH=7.0).

Example 6

Protein Structure Characterization and Thermostability

The secondary structure of the water-soluble variant was determined through circular dichroism (CD). Circular dichroism (CD) spectra were recorded by using CD Spectrometer (Chirascan, AppliedPhotophysics Limited, Leatherhead, United Kingdom) with a scan speed of 1 nm/s and 1 mm path length. Corresponding blanks were used for calibration for each assay and subtracted from raw data. Two data sets were recorded and averaged to increase the signal-to-noise ratio. The CDNN CD spectra deconvolution software was utilized to determine the secondary structure content of the proteins. CD spectroscopy for wsMUR-TM at different temperatures were recorded with 6 µM of the receptor in buffer (5 mM sodium phosphate, pH=7.0) from 10° C. to 90° C. in increments of 2° C. per min. Absorbance was maintained lower than 1.0 to ensure sufficient light transmission. The temperature-dependence curve was plotted using GraphPad Prism® (version 5, GraphPad Software, Inc. La Jolla).

The CD spectra indicated predominantly helical structures with a helical secondary structure content of ~48% (estimations based on the molar ellipticity over the range 205 to 260 nm). The comparison of the helical content with that of the native human MUR expressed in yeast system in the presence of high concentration of detergent (0.1% SDS) is presented in Table 1.

TABLE 1

Helical content comparison for the native and engineered receptors

Figure 14:
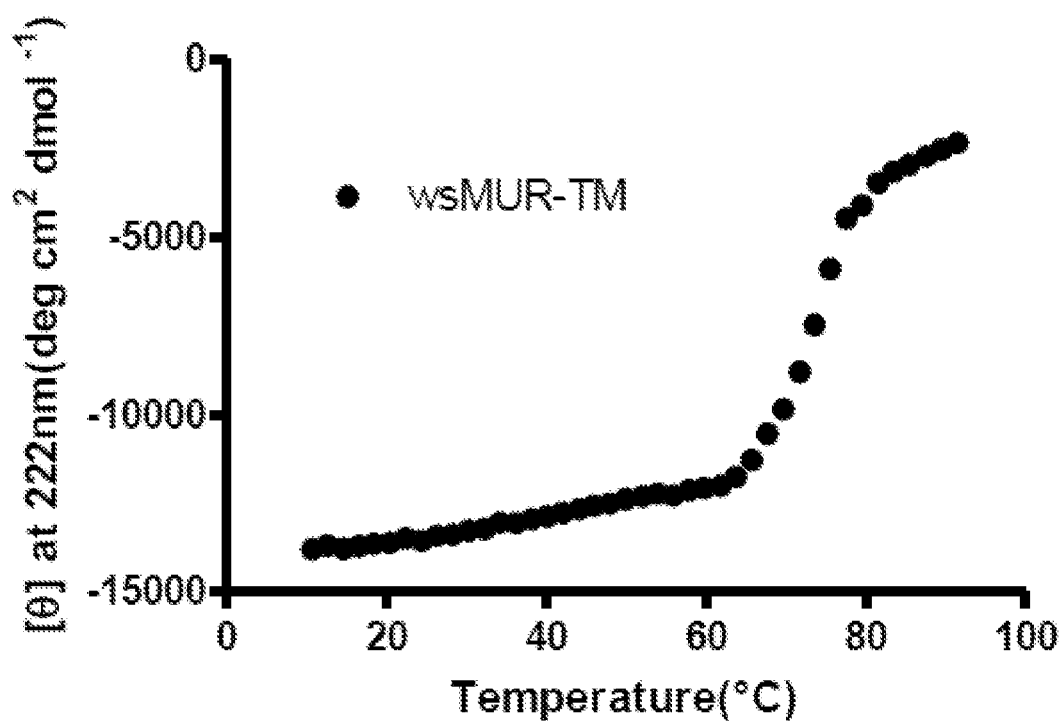
FIG. 14. Mean residue ellipticity at 222 nm of wsMUR-TM in buffer solution (5 mM sodium phosphate, pH=7.0) as a function of temperature, from 10 to 90° C. The spectrum of wsMUR-TM showed significant change near 62° C. and an almost complete loss in molar ellipticity at 90° C.
Figure 15:
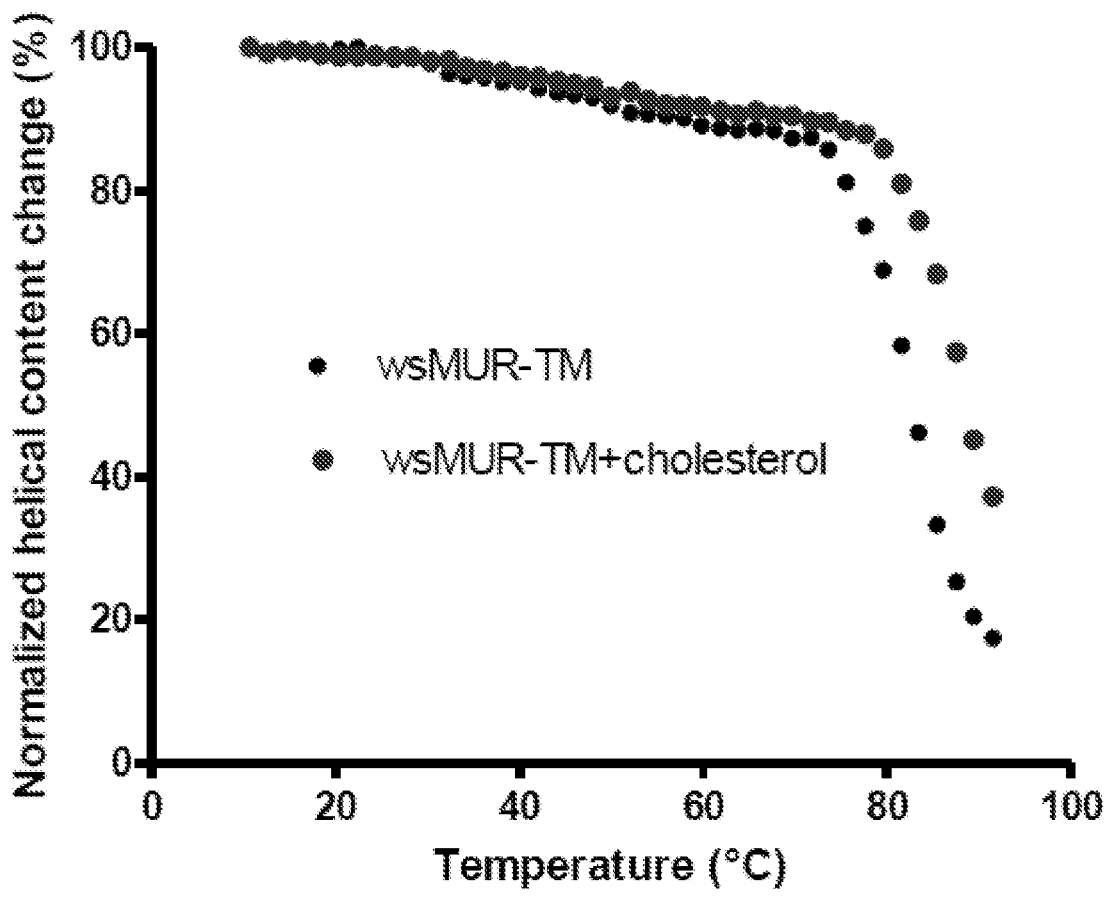

| 205-260 nm | wsMUR-TM (pH 7.0 in NaHPO$_4$) | Native MUR (pH 7.0 + 0.1% SDS) |
|---|---|---|
| Helix | 48.0% | 40.6% |
| Turn | 14.6% | 18.9% |
| Others | 37.4% | 40.5% | wsMUR-TM: transmembrane-only water-soluble human mu receptor variant;
MUR: human µ receptor As monitored by CD, wsMUR-TM started to lose ellipticity significantly near 62° C. and was almost fully unfolded at 90° C. (FIG. 14). The stability of wsMUR-TM was also investigated upon addition of cholesterol, which has been found to modulate the stability of several GPCRs. The inclusion of cholesterol caused a shift of the melting point from 82.9° C. to 89.3° C., suggesting that it may stabilize the helical structure of wsMUR-TM (FIG. 15).

CD and intrinsic tryptophan fluorescence were used to probe disulfide bond formation in the water-soluble variant.

The structure of wsMUR-TM was monitored with increasing concentrations of urea and the reducing agent 2-mercaptoethanol (2-ME). After addition of urea, the molar ellipticity at 222 nm and the intensity of the intrinsic tryptophan fluorescence of wsMUR-TM decreased. Even in 8 M urea, the protein retains some helical structure (Table 2). Upon addition of 2-ME, both the molar ellipticity and fluorescence further decreased, becoming more pronounced at the higher concentration of the reducing agent (200 mM). Thus the presence of an intramolecular disulfide bond is corroborated in the case of wsMUR-TM.

TABLE 2

Effects of denaturant and reducing agent on the wsMUR-TM

|  | None | Urea (8M) | Urea (8M) 2-ME (25 mM) | Urea (8M) 2-ME (200 mM) |
|---|---|---|---|---|
| Molar Ellipticity (%; 222 nm) | 100.0 | 40.0 | 25.1 | 0.0 |
| Fluorescence Peak Intensity (%; 300-350 nm) | 100.0 | 28.4 | 23.9 | 4.5 | wsMUR-TM: transmembrane-only water-soluble human μ receptor variant; Values are normalized to the condition without denaturant or reducing agent (None).
2-ME: 2-mercaptoethanol.

Intrinsic tryptophan fluorescence was used to provide qualitative information of the conformations adopted by the water-soluble receptors; wsMUR-TM contains just six tryptophan residues (W135$^{2.69}$, W194$^{4.50}$, W228$^{EC2}$, w230$^{EC2}$, W295$^{6.48}$, and W320$^{7.35}$). Of particular interest are the tryptophan residues located in the partially buried transmembrane locations of the model structure (positions 194, 295, and 320). The fluorescence associated with these residues is expected to be sensitive to the local hydrophobic environment and overall folding of the protein. The observed decrease in the tryptophan fluorescence and the red shift in the emission with increasing denaturant (urea) concentration suggest that at least some of these tryptophan residues are located in the interior of the protein.

The decrease of the tryptophan fluorescence under denaturing conditions and in the presence of 2-ME is consistent with the changes in CD spectra observed under similar conditions. The requirement of the reducing agent to fully denature and unfold the protein indicates the relevance of an intramolecular disulfide bond in stabilizing the receptor structure. Although these observations suggest the presence of a disulfide bond, they do not specify which bond is formed given the existence of 11 cysteine residues in wsMUR-TM. However, the CD and ligand-binding studies are consistent with the adoption of the proper protein tertiary structure and by extension with the formation of the correct disulfide bond.

Example 7

Ligand Binding Properties of the wsMUR-TM

Figure 16:
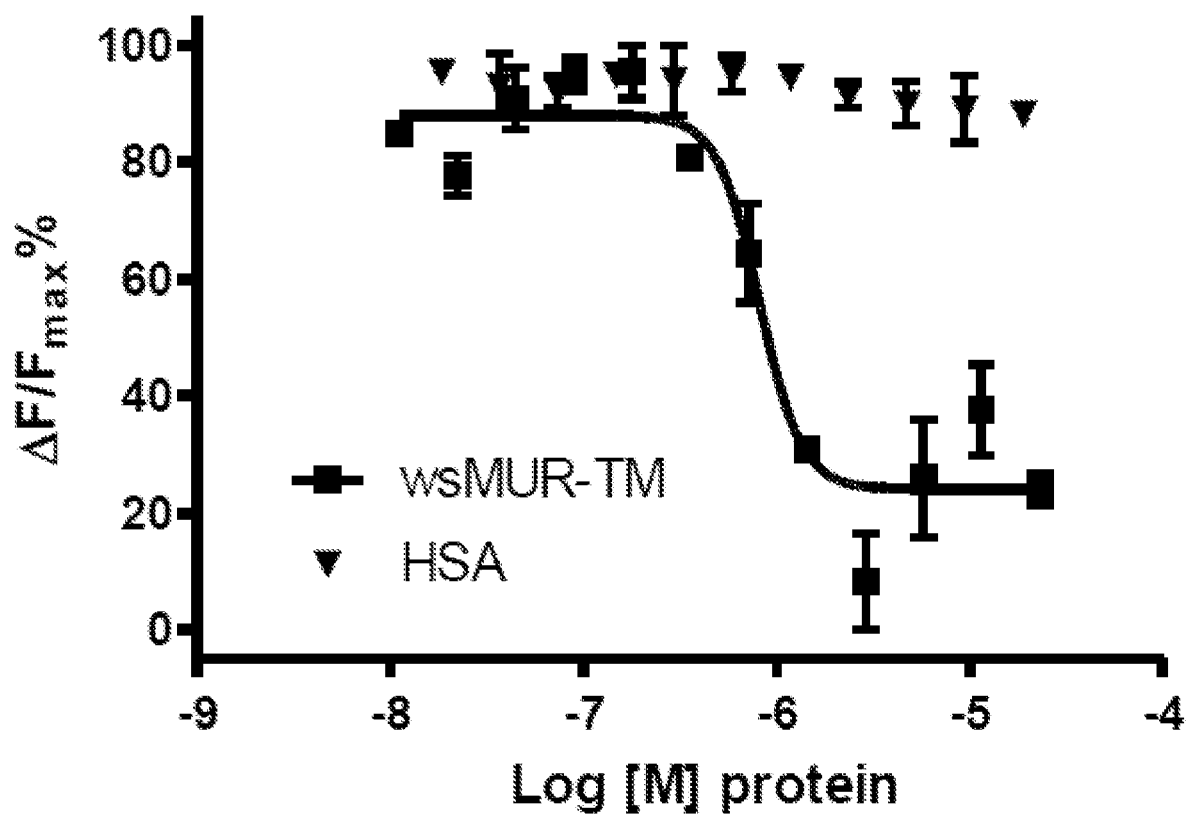
FIG. 16. Binding competition assay between the human μ opioid receptor expressed in HEK293 cells and the μ opioid water-soluble variants Inhibition of the native μ opioid receptor constitutive signal in the presence of increasing concentrations of wsMUR-FL (dots, $IC_{50}=8.4\times10^{-7}$ M, $R^2=0.9306$) or wsMUR-TM (squares, $IC_{50}=8.6\times10^{-7}$M, $R^2=0.9067$) in sodium phosphate buffer. Data for the negative control is also included, HSA (inverted triangles). Data is used to calculate HTRF ratios, and represent the mean±standard error of mean of quadruplicates. ΔF is used for the comparison of different runs of the same assay which reflects the signal to background of the assay. ΔF= [(Ratio$_{sample}$−Ratio$_{backgroud}$)/Ratio$_{backgroud}$](%).
Figure 17:
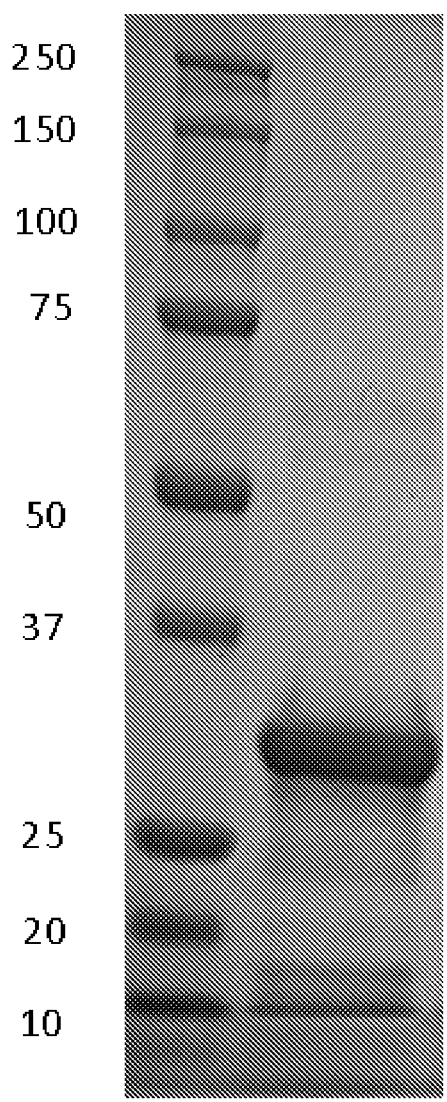
FIG. 17. Expression and purification of wsMUR-TM (SEQ ID NO: 2)
Figure 18:
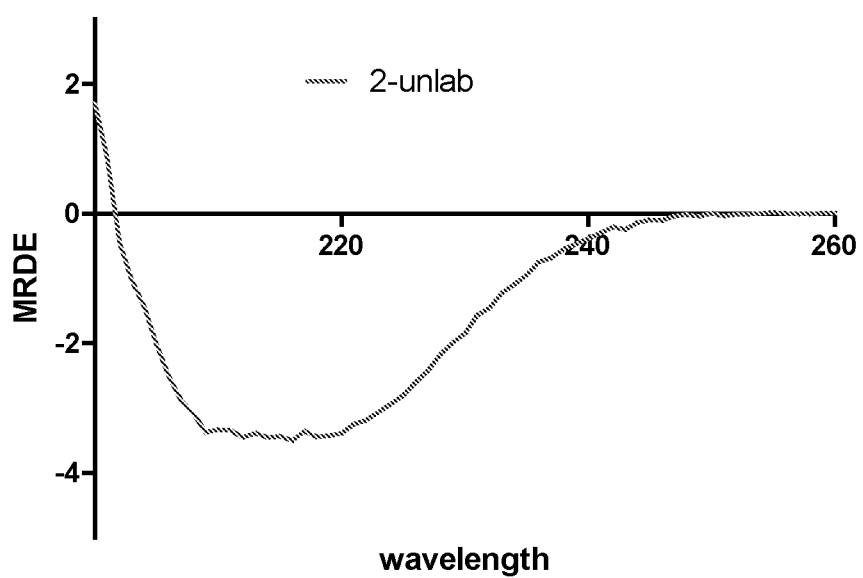
FIG. 18. The secondary structure of wsMUR as indicated by CD spectra analysis.

A recently developed methodology which uses a fluorescently labeled ligand and the native MUR was used to investigate the ligand-binding capabilities of the water-soluble receptors. Naltrexone binding was monitored using a competitive TR-FRET (time-resolved fluorescence resonance energy transfer) based assay with fluorescently labeled wild type MUR and a naltrexone-derived antagonist. The ratio of fluorescence emission at 665 nm and 620 nm decreased in a dose-dependent manner with increasing concentrations of wsMUR-TM. The determined $K_d$ values for naltrexone were 65±1.8 nM (wsMUR-TM) (FIG. 16). As a negative control, human serum albumin (HSA, a soluble helical protein), rather than a water-soluble variant, was introduced with no significant change in the fluorescence ratio upon HSA addition.

This binding assay has been applied to study several GPCRs and particularly MUR, where the $K_i$ values for the morphinan opioids naloxone and naltrindole were estimated (5.1 nM and 8.1 nM for naloxone and naltrindole, respectively) and found to be in agreement with values obtained using other techniques, wsMUR-TM competes with native MUR expressed in HEK293 cells for the potent opioid antagonist naltrexone. This study demonstrates that the wsMUR-TM can compete with the native MUR for the fluorescent antagonist with binding affinities in nM range. The HSA (negative control) results indicate that the interaction of the water-soluble variant with naltrexone is selective and specific.

Example 8

Additional MUR Constructs

Figure 19:
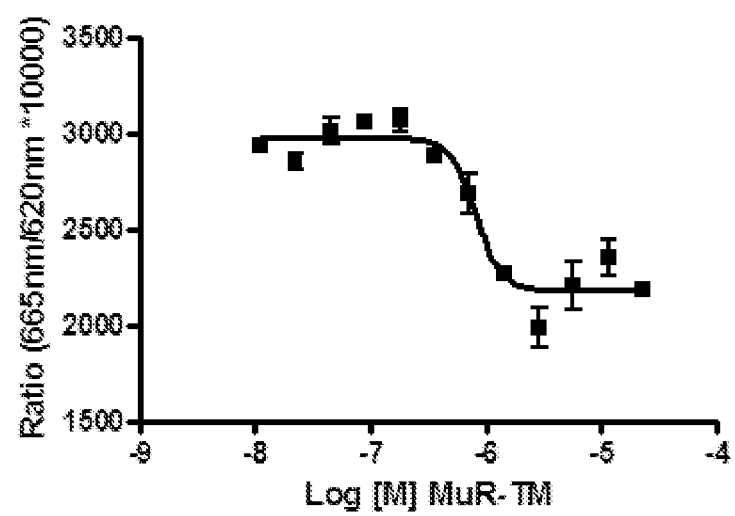
FIG. 19. The specific interaction of naltrexone with the wsMUR, similar to that indicated in FIG. 16.
Figure 20:
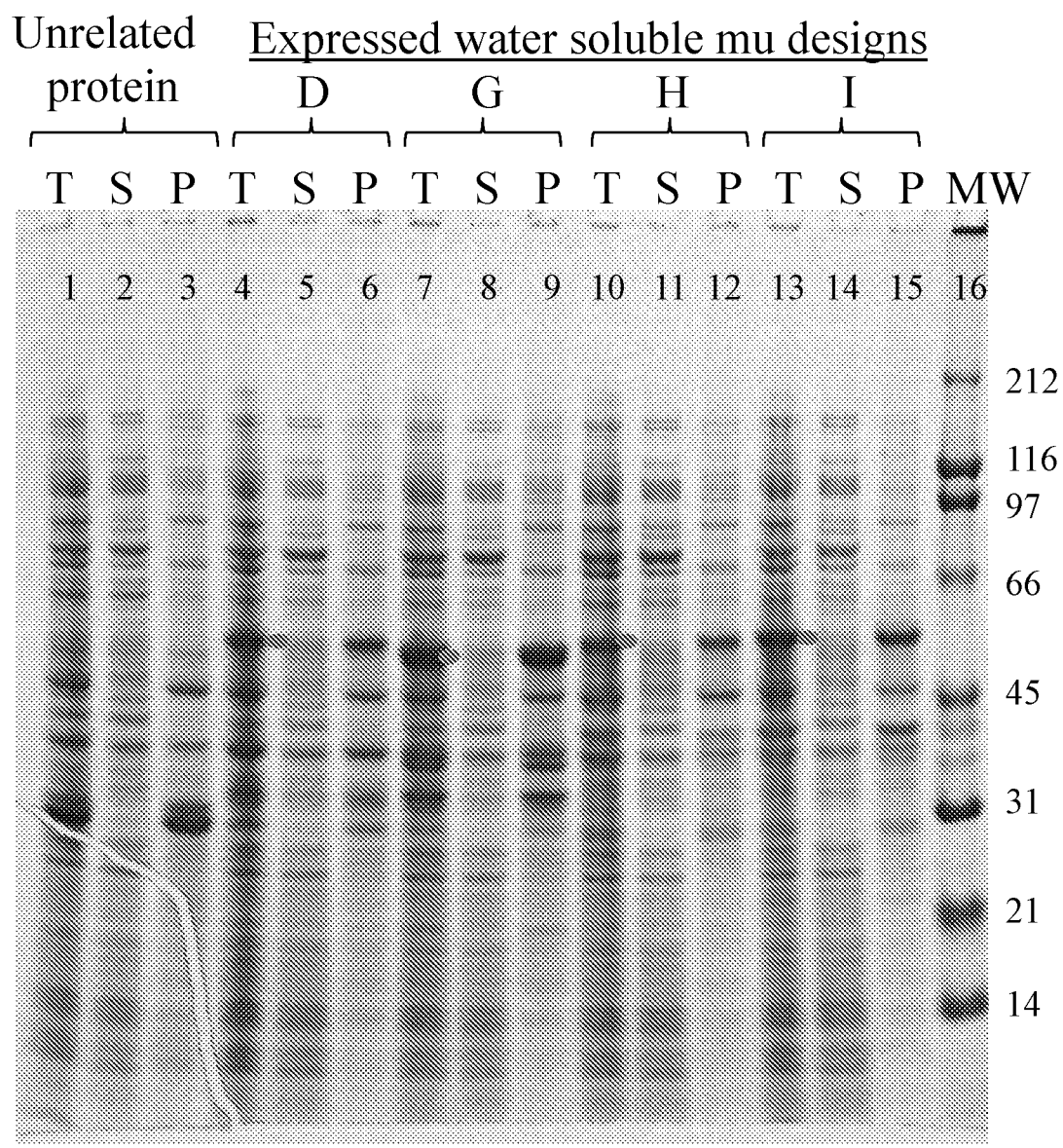
FIG. 20. Expression of 4 different versions of the wsMURs (SEQ ID NOs: 3-6). All 4 version of the receptors are expressed well in *E. Coli* and were purified successfully using affinity chromatography.
Figure 21:
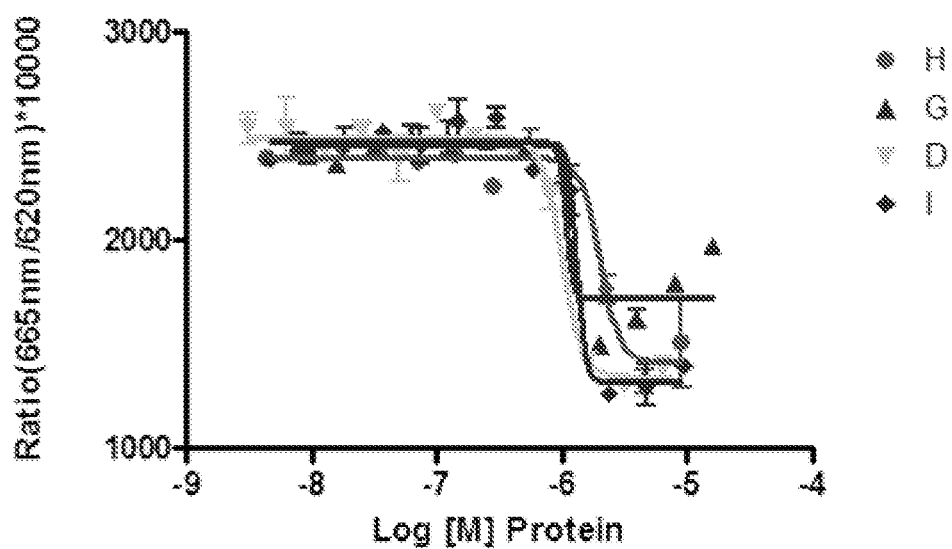
FIG. 21. Four versions of the wsMUR demonstrate comparable affinities with naltrexone by using the methodology described for FIG. 16.

Constructs having unique sequences, but similar properties to the wsMUR-TM construct were also produced and analysed as described above. One such construct is a second wsMUR recombinant protein (wsMUR-TM+7mut-SEQ ID NO: 2). Studies performed to characterize wsMUR-TM+7mut demonstrate its production and isolation using bacterial expression (FIG. 15), its alpha-helical nature as measure by CD (FIG. 16), and binding activity was also observed for related MUR constructs wsMUR-TM+7mut (FIG. 19). Similar characteristics were observed for the MUR constructs G-min (SEQ ID NO: 3), H-min (SEQ ID NO: 4), I-min (SEQ ID NO: 5), and D-min (SEQ ID NO: 7) (see FIGS. 20 and 21).

Example 9

Production and Isolation of a Water-Soluble

Human Beta$_2$ Adrenergic Receptor

Figure 22:
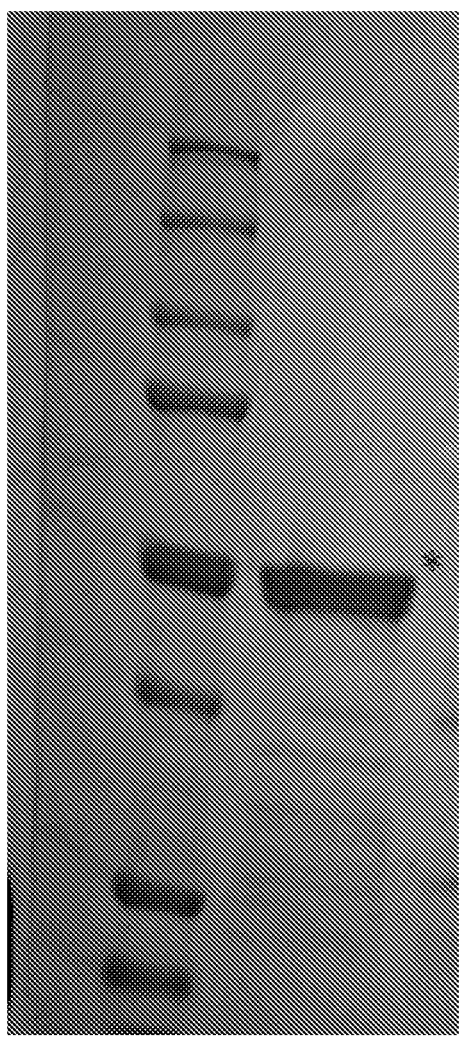
FIG. 22. Expression and purification of a water-soluble variant of the beta2-adrenergic receptor.
Figure 23:
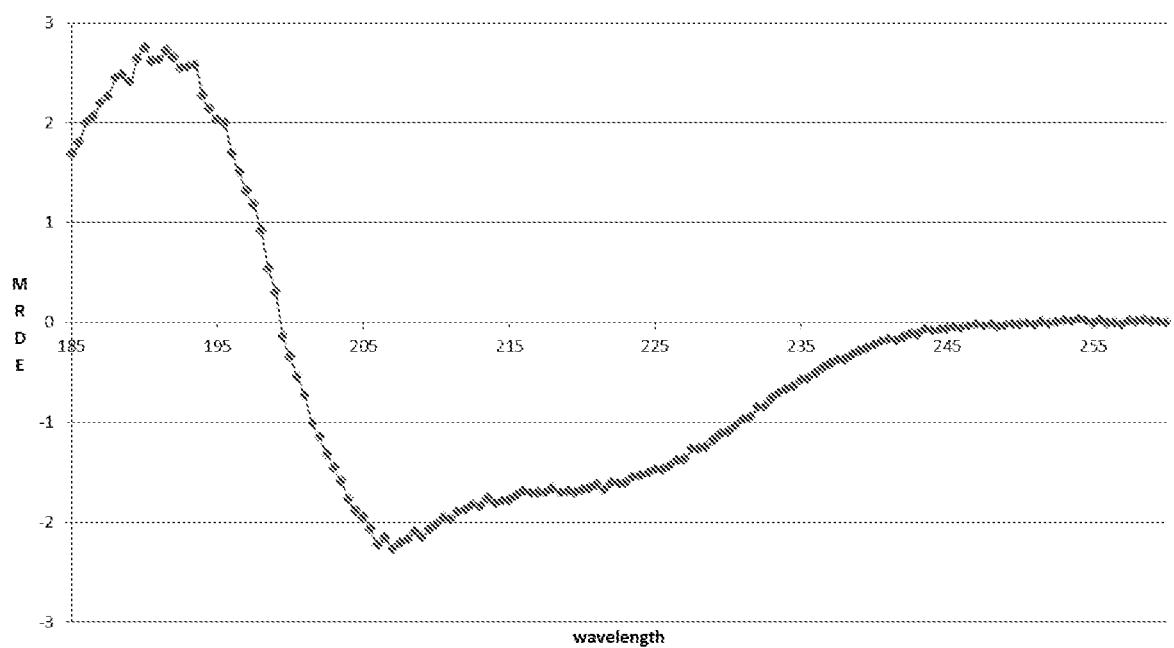
FIG. 23. The secondary structure of the water soluble beta2-adrenergic receptor as indicated by the CD spectra analysis.

Studies were conducted to engineer and generate a more water soluble human β$_2$ adrenergic receptor (BAD). After analyzing the native protein sequence, as described above for MUR, amino acid sequence changes were made to cause the engineered BAR to be less hydrophobic. Two recombinant BAR sequences were designed (SEQ ID NOs: 7 and 8). To assess expression and isolation from bacteria, *E. coli* were transformed with a construct encoding SEQ ID NO: 8 (BAD4), cultured and then lysed. BAD4 was identified on a western blot following purification from the bacterial cell lysate (FIG. 22). The isolated protein was also assessed for helical structural content by CD spectroscopy and was shown to have a spectral profile consistent with high alpha-helical content (FIG. 23).

Example 10

GFET Functionalization

GFET devices (e.g., those of the type in the array of Example 1) may be functionalized on the graphene surface with molecules, such as antibodies, antibody fragments, computationally designed receptor proteins, or any combination thereof, to form biosensors.

In one exemplary embodiment, graphene may be functionalized through the use of a pyrene compound, e.g., 1-pyrene butanoic acid succinimidyl ester ("PYR-NHS"). The pyrene portion of the molecule interacts with the graphene through non-covalent pi-pi stacking interaction. The NHS ester portion of the molecule can remain available for use in functionalization with molecules. Molecules with an accessible amine group can displace the NHS ester portion of the PYR-NHS to form an amide bond; other displacement reactions may also be used to form bonds. Measurements indicate that the mobility of the graphene is unaffected by the functionalization method described. Biosensor function, when compared to the biosensors made according to methods described in Example 2, is otherwise unaltered.

In another exemplary embodiment, graphene is functionalized through the use of Ni-nitrilotriacetic acid (Ni-NTA). In this embodiment, the $Ni^{2+}$ cations can bind to histidine tags of recombinant proteins. Thus, the present disclosure provides methods of functionalizing a graphene field effect transistor having a graphene layer. These methods may include exposing the graphene layer to a first molecule so as to form pi-pi stacking bonds between a portion of the first molecule and the graphene; and displacing a portion of the first molecule via a displacement reaction so as to form a covalent bond between the graphene layer and a detection molecule.

When ranges are used herein for physical properties, such as molecular weight, or chemical properties, such as chemical formulae, all combinations, and subcombinations of ranges for specific embodiments therein are intended to be included.

The disclosures of each patent, patent application, and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A sensing device, comprising
a graphene portion placing first and second electrodes into electronic communication with one another,
the graphene portion comprising a detection molecule bonded thereto, and being characterized as having a D peak that is less than a G peak when assessed using Raman spectroscopy,
the detection molecule being in electronic communication with the graphene and being bound to the graphene portion by non-covalent pi-pi stacking interaction between the graphene and a 1-pyrene butanoic acid succinimidyl ester molecule and an amide bond between the 1-pyrene butanoic acid succinimidyl ester molecule and the detection molecule, and,
the detection molecule being an integral membrane receptor molecule comprising a water-soluble variant of a mu receptor capable of complementary binding to at least one target.

2. The sensing device of claim 1, the sensing device being configured such that the device, during operation, is capable of detecting a change in signal related to the complementary binding between the detection molecule at the at least one target.

3. The sensing device of claim 1, further comprising a voltage source configured to apply a voltage across the first and second electrodes.

4. A sensing device of claim 1, wherein the detection molecule comprises a protein having an amino acid sequence that is at least about 95% identical to any one of SEQ ID 1 through SEQ ID 9.

5. A multiplexed device, comprising:
a substrate having a plurality of sensing devices according to claim 1 disposed thereon, at least two of the sensing device comprising different detection molecules.

6. The sensing device of claim 1, wherein the detection molecule comprises protein UniProtKB: P07550 or an associated variant with the capability to bind opioid ligands.

7. A sensing device, comprising:
a graphene portion placing first and second electrodes into electronic communication with one another,
the graphene portion comprising a detection molecule bonded thereto, and being characterized as having a D peak that is less than a G peak when assessed using Raman spectroscopy,
the detection molecule being in electronic communication with the graphene,
the detection molecule being a recombinant integral membrane protein molecule comprising a water-soluble variant of a mu receptor capable of complementary binding to at least one target.

* * * * *

SEQUENCE LISTING

```
<160> NUMBER OF SEQ ID NOS: 16

<210> SEQ ID NO 1
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser Met Ile Thr Ala Ile Lys Ile His Glu Glu Tyr Lys Lys Val Cys
1               5                   10                  15

Glu Glu Gly Lys Lys Gly Asn Lys Leu Val Met Glu Val Ile Val Arg
            20                  25                  30

Tyr Thr Lys Met Lys Thr Ala Thr Asn Ile Tyr Ile Phe Asn Leu Ala
        35                  40                  45

Lys Ala Asp Ala Leu Ala Glu Ser Thr Leu Pro Phe Gln Ser Val Asn
    50                  55                  60

Lys Leu Met Gly Thr Trp Pro Phe Gly Thr Ile Leu Cys Lys Lys Val
65                  70                  75                  80

Ile Ser Ile Asp Tyr Tyr Asn Met Phe Thr Ser Ile Phe Thr Leu Cys
                85                  90                  95

Thr Met Ser Val Asp Arg Tyr Ile Ala Val Cys His Pro Val Lys Ala
            100                 105                 110

Leu Asp Phe Arg Thr Pro Arg Asn Ala Lys Glu Glu Asn Glu Lys Asn
        115                 120                 125

Trp Lys Leu Ser Ser Glu Ile Gly Lys Pro Val Glu Lys Lys Ala Thr
    130                 135                 140

Thr Lys Tyr Arg Gln Gly Ser Ile Asp Cys Thr Leu Thr Phe Ser His
145                 150                 155                 160

Pro Thr Trp Tyr Trp Glu Asp Lys Leu Lys Asp Glu Val Phe Lys Lys
                165                 170                 175

Ala Phe Glu Glu Pro Val Lys Lys Ile Lys Glu Cys Tyr Gly Leu Met
            180                 185                 190

Ile Leu Arg Leu Lys Ser Val Arg Met Leu Ser Gly Ser Lys Glu Lys
        195                 200                 205
```

```
Asp Arg Asn Leu Arg Arg Ile Thr Arg Met Val Leu Val Val Glu
    210                 215                 220

Val Phe Ile Lys Cys Trp Thr Glu Ile His Lys Tyr Val Lys Glu Gly
225                 230                 235                 240

Lys Leu Val Thr Ile Pro Glu Thr Thr Phe Gln Thr Val Ser Trp His
                245                 250                 255

Glu Cys Ile Ala Lys Gly Tyr Lys Asn Ser Cys Glu Asn Pro Lys Leu
                260                 265                 270

Tyr Glu Glu Leu Asp Glu Asn Phe Lys Arg Cys Phe Arg Glu Phe Cys
                275                 280                 285

<210> SEQ ID NO 2
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ser Met Ile Thr Ala Ile Lys Ile Leu Glu Glu Tyr Lys Lys Val Cys
1               5                   10                  15

Glu Glu Gly Arg Lys Gly Asn Lys Leu Val Met Glu Val Ile Val Arg
                20                  25                  30

Tyr Thr Lys Met Lys Thr Ala Thr Asn Ile Tyr Ile Phe Asn Leu Ala
                35                  40                  45

Lys Ala Asp Ala Leu Ala Glu Ser Thr Leu Pro Phe Gln Ser Val Asn
50                  55                  60

Lys Leu Met Gly Thr Trp Pro Phe Gly Thr Ile Leu Cys Lys Lys Val
65                  70                  75                  80

Ile Ser Ile Asp Tyr Tyr Asn Met Phe Thr Ser Ile Phe Thr Leu Cys
                85                  90                  95

Thr Met Ser Val Asp Arg Tyr Ile Ala Val Cys His Pro Val Lys Ala
                100                 105                 110

Leu Asp Phe Arg Thr Pro Arg Asn Ala Lys Glu His Asn Glu Lys Asn
                115                 120                 125

Trp Lys Leu Ser Ser Glu Ile Gly Lys Pro Val Glu Lys Arg Ala Thr
130                 135                 140

Thr Lys Tyr Arg Gln Gly Ser Ile Asp Cys Thr Leu Thr Phe Ser His
145                 150                 155                 160

Pro Thr Trp Tyr Trp Glu Asp Lys Leu Lys Asp Thr Val Phe Lys Lys
                165                 170                 175

Ala Phe Glu Glu Pro Val Lys Val Ile Lys Glu Cys Tyr Gly Leu Met
                180                 185                 190

Ile Leu Arg Leu Lys Ser Val Arg Met Leu Ser Gly Ser Lys Glu Lys
                195                 200                 205

Asp Arg Asn Leu Arg Arg Ile Thr Arg Met Val Leu Val Val Val Glu
                210                 215                 220

Val Phe Ile Lys Cys Trp Thr Glu Ile His Lys Tyr Val Lys Glu Gly
225                 230                 235                 240

Lys Leu

<210> SEQ ID NO 3
<211> LENGTH: 288
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 3

```
Ser Glu Lys Lys Arg Glu Lys Ile Phe Gln Glu Tyr Lys Lys Val Tyr
1               5                   10                  15

Glu Glu Gly Lys Glu Gly Asn Lys Leu Val Val Asp Val Ile Glu Arg
            20                  25                  30

Tyr Thr Lys Met Lys Thr Ala Thr Asn Asp Tyr Ile Arg Asn Leu Ala
        35                  40                  45

Glu Ala Asp Met Lys Ala Thr Glu Thr Leu Pro Tyr Gln Ser Glu Asn
50                  55                  60

Tyr Leu Lys Gly Thr Trp Pro Phe Gly Thr Glu Glu Cys Lys Lys Val
65                  70                  75                  80

Ile Ser Gln Asp Tyr Tyr Asn Met Phe Thr Ser Ile Glu Thr Leu Lys
                85                  90                  95

Thr Met Ser Glu Asp Arg Tyr Ile Ala Val Glu His Pro Val Lys Ala
            100                 105                 110

Leu Asp Phe Arg Thr Pro Arg Asp Ala Gln Glu Lys Asn Lys Glu Asn
        115                 120                 125

Trp Glu Lys Ser Lys Lys Ile Gly Glu Pro Val Glu Lys Ser Ala Thr
130                 135                 140

Thr Lys Tyr Arg Gln Gly Ser Ile Asp Cys Thr Leu Thr Phe Ser His
145                 150                 155                 160

Pro Thr Trp Tyr Trp Glu Asn Lys Gln Lys Gln Lys Val Phe Glu Glu
                165                 170                 175

Ala Phe Lys Lys Pro Val Glu Glu Ile Lys Lys Lys His Glu Glu Met
            180                 185                 190

Gln Lys Arg Leu Lys Ser Val Arg Met Leu Ser Gly Ser Lys Glu Lys
        195                 200                 205

Asp Arg Asn Leu Arg Arg Ile Thr Arg Met Val Met Glu Val Val Gln
210                 215                 220

Val Phe Ile Lys His Trp Asp Pro Ile His Lys Tyr Val Lys Asp Lys
225                 230                 235                 240

Ala Glu Lys Thr Ile Pro Glu Thr Thr Phe Gln Thr Lys Lys Trp His
                245                 250                 255

Glu Ser Ile Ile Glu Gly Tyr Lys Asn Ser Asp His Asn Pro Lys Leu
            260                 265                 270

Tyr Asp Glu Asn Asp Gly Asn Phe Lys Arg His Phe Arg Glu Phe Lys
        275                 280                 285
```

<210> SEQ ID NO 4
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Ser Glu Lys Lys Lys Glu Glu Ile Trp Lys Gly Tyr Lys Glu Trp Ile
1               5                   10                  15

Glu Lys Gly Lys Lys Gly Asn Lys Leu Val Met Glu Val Ile Glu Arg
            20                  25                  30

Tyr Thr Lys Met Lys Thr Ala Thr Asn Asp Tyr Ile Lys Asn Leu Ala
        35                  40                  45
```

Glu Ala Asp Trp Lys Ala Thr Glu Thr Leu Pro Gln Ser Lys Asn
            50                  55                  60

Tyr Leu Glu Gly Thr Trp Pro Phe Gly Lys Glu Lys Cys Lys Glu Val
 65                  70                  75                  80

Ile Ser Arg Asp Tyr Tyr Asn Met Phe Thr Ser Ile Tyr Thr Leu Lys
                 85                  90                  95

Thr Met Ser Lys Asp Arg Tyr Ile Ala Val Asp His Pro Val Lys Ala
            100                 105                 110

Leu Asp Phe Arg Thr Pro Arg Glu Ala Lys Lys Glu Asn Lys Lys Asn
            115                 120                 125

Trp Glu Glu Ser Lys Lys Ile Gly Glu Pro Val Lys Lys Asp Ala Thr
            130                 135                 140

Thr Lys Tyr Arg Gln Gly Ser Ile Asp Cys Thr Leu Thr Phe Ser His
145                 150                 155                 160

Pro Thr Trp Tyr Trp Glu Asn Lys Gln Lys Glu Glu Val Phe Lys Lys
                165                 170                 175

Ala Phe Glu Glu Pro Val Lys Asp Ile Glu Glu Gln Lys Lys Lys Met
            180                 185                 190

Asp Glu Arg Leu Lys Ser Val Arg Met Leu Ser Gly Ser Lys Glu Lys
            195                 200                 205

Asp Arg Asn Leu Arg Arg Ile Thr Arg Met Val Trp Glu Val Val Lys
            210                 215                 220

Lys Phe Phe Glu Lys Trp Lys Pro Ile His Glu Val Lys Lys Lys
225                 230                 235                 240

Ala Glu Lys Thr Ile Pro Glu Thr Thr Phe Gln Thr Glu Glu Trp His
                245                 250                 255

Lys Lys Ile Tyr Glu Gly Tyr Lys Asn Ser Glu Glu Asn Pro Lys Leu
            260                 265                 270

Tyr Asp Glu Lys Asp Glu Asn Phe Lys Arg Glu Phe Arg Glu Phe Glu
            275                 280                 285

<210> SEQ ID NO 5
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Glu Glu Lys Lys Lys Lys Ile Asp Glu Glu Tyr Lys Lys Gln Ile
 1               5                  10                  15

Glu Glu Gly Lys Lys Gly Asn Lys Leu Val Glu Asp Val Ile Glu Arg
                20                  25                  30

Tyr Thr Lys Met Lys Thr Ala Thr Asn Ile Tyr Ile Lys Asn Leu Ala
            35                  40                  45

Gln Ala Asp Gln Gly Ala Thr Lys Thr Leu Pro Glu Gln Ser Lys Asn
            50                  55                  60

Tyr Leu Glu Gly Thr Trp Pro Phe Gly Lys Lys Cys Lys Glu Val
 65                  70                  75                  80

Ile Ser Lys Asp Tyr Tyr Asn Met Phe Thr Ser Ile Trp Thr Leu Asp
                 85                  90                  95

Thr Met Ser Glu Asp Arg Tyr Ile Ala Val Glu His Pro Val Lys Ala
            100                 105                 110

Leu Asp Phe Arg Thr Pro Arg Lys Ala Lys Glu Glu Asn Lys Lys Asn

```
            115                 120                 125
Trp Glu Glu Ser Lys Lys Ile Gly Glu Pro Val Lys Lys Glu Ala Thr
        130                 135                 140

Thr Lys Tyr Arg Gln Gly Ser Ile Asp Cys Thr Leu Thr Phe Ser His
145                 150                 155                 160

Pro Thr Trp Tyr Trp Glu Asn Lys Trp Lys Glu Val Phe Lys Lys
                    165                 170                 175

Ala Phe Glu Glu Pro Val Lys Lys Ile Glu Arg Lys Lys Lys Met
                180                 185                 190

Glu Glu Arg Leu Lys Ser Val Arg Met Leu Ser Gly Ser Lys Glu Lys
                195                 200                 205

Asp Arg Asn Leu Arg Arg Ile Thr Arg Met Val Glu Asn Val Val Lys
        210                 215                 220

Arg Phe Glu Glu His Trp Lys Pro Ile His Glu Arg Val Lys Glu Lys
225                 230                 235                 240

Ala Lys Lys Thr Ile Pro Glu Thr Thr Phe Gln Thr Glu Glu Trp His
                    245                 250                 255

Lys Glu Ile Gln Lys Gly Tyr Glu Asn Ser Lys Glu Asn Pro Lys Leu
                260                 265                 270

Tyr Glu Lys Glu Asp Glu Asn Phe Lys Arg Glu Phe Arg Glu Phe Lys
                275                 280                 285

<210> SEQ ID NO 6
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ser Glu Glu Thr Ala Glu Ile Glu Lys Gln Tyr Lys Glu Val Ile
1               5                   10                  15

Glu Lys Gly Lys Lys Gly Asn Lys Leu Val Lys Glu Val Ile Glu Arg
                20                  25                  30

Tyr Thr Lys Met Lys Thr Ala Thr Asn Ile Tyr Ile Trp Asn Leu Ala
            35                  40                  45

Glu Ala Asp Leu Lys Ala Thr Glu Thr Leu Pro Lys Gln Ser Gln Asn
        50                  55                  60

Tyr Leu Glu Gly Thr Trp Pro Phe Gly Gln Glu Asp Cys Lys Asn Val
65                  70                  75                  80

Ile Ser Ile Asp Tyr Tyr Asn Met Phe Thr Ser Ile Trp Thr Leu Ala
                85                  90                  95

Thr Met Ser Glu Asp Arg Tyr Ile Ala Val Ala His Pro Val Lys Ala
            100                 105                 110

Leu Asp Phe Arg Thr Pro Arg Glu Ala Glu Lys Glu Asn Lys Lys Asn
        115                 120                 125

Trp Glu Glu Ser Lys Lys Ile Gly Glu Pro Val Lys Lys Asp Ala Thr
        130                 135                 140

Thr Lys Tyr Arg Gln Gly Ser Ile Asp Cys Thr Leu Thr Phe Ser His
145                 150                 155                 160

Pro Thr Trp Tyr Trp Glu Asn Asp Leu Lys Asp Asp Val Phe Lys Lys
                    165                 170                 175

Ala Phe Glu Glu Pro Val Lys Lys Ile Glu Glu Ala Tyr Lys Lys Met
                180                 185                 190
```

-continued

Gln Glu Arg Leu Lys Ser Val Arg Met Leu Ser Gly Ser Lys Glu Lys
            195                 200                 205

Asp Arg Asn Leu Arg Arg Ile Thr Arg Met Val Trp Lys Val Val Gln
210                 215                 220

Ile Phe Ile Glu Ala Trp Asp Pro Ile His Lys Tyr Val Ile Glu Lys
225                 230                 235                 240

Ala Lys Glu Thr Ile Pro Glu Thr Thr Phe Gln Thr Glu Glu Trp His
            245                 250                 255

Lys Ser Ile Ala Glu Gly Tyr Lys Asn Ser Ala Glu Asn Pro Glu Leu
            260                 265                 270

Tyr Lys Lys Asp Asp Glu Asn Phe Lys Arg Thr Phe Arg Glu Phe Glu
            275                 280                 285

<210> SEQ ID NO 7
<211> LENGTH: 422
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala His His His His His His Val Met Gly Gln Pro Gly Asn Gly
1               5                   10                  15

Ser Ala Phe Leu Leu Ala Pro Asn Gly Ser His Ala Pro Asp His Asp
            20                  25                  30

Val Thr Gln Gln Arg Asp Glu Glu Trp Val Lys Gly Gln Gly Lys Lys
        35                  40                  45

Met Ser Glu Ile Val Lys Lys Ile Val Glu Gly Asn Lys Leu Val Ile
50                  55                  60

Thr Ala Ile Lys Lys Phe Glu Arg Leu Gln Thr Val Thr Asn Tyr Phe
65                  70                  75                  80

Ile Thr Ser Leu Ala Glu Ala Asp Leu Lys Met Gly Glu Ala Val Val
            85                  90                  95

Pro Tyr Gly Ala Ala His Ile Leu Lys Lys Met Trp Thr Tyr Gly Asn
            100                 105                 110

Lys Trp Cys Glu Tyr Trp Thr Ser Ile Asp Val Leu Thr Val Thr Ala
            115                 120                 125

Ser Ile Glu Thr Leu Asp Val Ile Ala Glu Asp Arg Tyr Lys Ala Ile
            130                 135                 140

Thr Ser Pro Phe Lys Tyr Gln Ser Glu Leu Thr Lys Asn Lys Ala Arg
145                 150                 155                 160

Glu Glu Ile Lys Lys Val Trp Glu Arg Ser Gly Lys Thr Ser Phe Asp
            165                 170                 175

Pro Ile Gln Lys His Lys Tyr Arg Ala Thr His Gln Glu Ala Ile Asn
            180                 185                 190

Cys Tyr Ala Asn Glu Thr Cys Cys Asp Phe Phe Thr Asn Gln Asp Tyr
            195                 200                 205

Ala Lys Lys Ser Ser Lys Glu Ser Phe Tyr Glu Pro Leu Lys Lys Met
            210                 215                 220

Lys Glu Val Tyr Ser Arg Val Glu Gln Glu Ala Lys Arg Gln Leu Gln
225                 230                 235                 240

Lys Ile Asp Lys Ser Glu Gly Arg Phe His Val Gln Asn Leu Ser Gln
            245                 250                 255

Val Glu Gln Asp Gly Arg Thr Gly His Gly Leu Arg Arg Ser Ser Lys
            260                 265                 270

```
Glu Ser Leu Lys Glu His Lys Ala Leu Lys Thr Leu Gly Glu Ile Met
            275                 280                 285
Gly Thr Phe Thr Lys Gln Trp Glu Pro Phe Phe Lys Val Asn Glu Glu
        290                 295                 300
His Val Lys Gln Asp Asn Lys Ile Arg Lys Glu Glu Tyr Ile Lys Leu
305                 310                 315                 320
Asn Trp Glu Gly Tyr Lys Asn Ser Gly Glu Asn Pro Lys Ile Tyr Glu
                325                 330                 335
Arg Ser Pro Asp Phe Arg Ile Ala Phe Gln Glu Leu Lys Ser Leu Arg
            340                 345                 350
Arg Ser Ser Leu Lys Ala Tyr Gly Asn Gly Tyr Ser Ser Asn Gly Asn
        355                 360                 365
Thr Gly Glu Gln Ser Gly Tyr His Val Glu Gln Glu Lys Glu Asn Lys
    370                 375                 380
Leu Leu Ala Glu Asp Leu Pro Gly Thr Glu Asp Phe Val Gly His Gln
385                 390                 395                 400
Gly Thr Val Pro Ser Asp Asn Ile Asp Ser Pro Gly Arg Asn Ala Ser
                405                 410                 415
Thr Asn Asp Ser Leu Leu
            420

<210> SEQ ID NO 8
<211> LENGTH: 422
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala His His His His His His Val Met Gly Gln Pro Gly Asn Gly
1               5                   10                  15
Ser Ala Phe Leu Leu Ala Pro Asn Gly Ser His Ala Pro Asp His Asp
            20                  25                  30
Val Thr Gln Gln Arg Asp Glu Glu Trp Val Lys Gly Thr Gly Arg Gln
        35                  40                  45
Met Ser Glu Ile Val Lys Lys Ile Val Glu Gly Asn Lys Leu Val Ile
    50                  55                  60
Thr Ala Ile Gln Lys Phe Glu Arg Leu Gln Thr Val Thr Asn Tyr Phe
65                  70                  75                  80
Ile Thr Ser Leu Ala Glu Ala Asp Leu Lys Met Gly Glu Ala Val Val
                85                  90                  95
Pro Tyr Gly Ala Ala His Ile Leu Lys Lys Met Trp Thr Tyr Gly Asn
            100                 105                 110
Arg Trp Cys Glu Tyr Trp Thr Ser Ile Asp Val Leu Thr Val Thr Ala
        115                 120                 125
Ser Ile Glu Thr Leu Asp Val Ile Ala Glu Asp Arg Tyr Lys Ala Ile
    130                 135                 140
Thr Ser Pro Phe Lys Tyr Gln Ser Glu Leu Thr Lys Asn Lys Ala Arg
145                 150                 155                 160
Glu Glu Ile Lys Lys Val Trp Glu Arg Ser Gly Lys Thr Ser Phe Asp
                165                 170                 175
Pro Ile Gln Lys His Lys Tyr Arg Ala Thr His Gln Glu Ala Ile Asn
            180                 185                 190
Cys Tyr Ala Asn Glu Thr Cys Cys Asp Phe Phe Thr Asn Gln Asp Tyr
```

```
                195                 200                 205
Ala Lys Lys Ser Ser Lys Gln Ser Phe Tyr Glu Pro Leu Gln Lys Met
210                 215                 220

Lys Asp Val Tyr Ser Arg Val Glu Gln Ala Lys Arg Gln Leu Gln
225                 230                 235                 240

Lys Ile Asp Lys Ser Glu Gly Arg Phe His Val Gln Asn Leu Ser Gln
            245                 250                 255

Val Glu Gln Asp Gly Arg Thr Gly His Gly Leu Arg Arg Ser Ser Lys
                260                 265                 270

Glu Ser Leu Lys Glu His Lys Ala Leu Lys Thr Leu Gly Glu Ile Met
            275                 280                 285

Gly Thr Phe Thr Arg Gln Trp Asp Pro Phe Phe Lys Val Asn Glu Glu
290                 295                 300

His Val Lys Gln Asp Asn Lys Ile Arg Lys Glu Tyr Ile Lys Leu
305                 310                 315                 320

Asn Trp Glu Gly Tyr Lys Asn Ser Gly Glu Asn Pro Lys Ile Tyr Glu
                325                 330                 335

Arg Ser Pro Asp Phe Arg Ile Ala Phe Gln Glu Leu Arg Ser Leu Arg
            340                 345                 350

Arg Ser Ser Leu Lys Ala Tyr Gly Asn Gly Tyr Ser Asn Gly Asn
        355                 360                 365

Thr Gly Glu Gln Ser Gly Tyr His Val Glu Gln Glu Lys Glu Asn Lys
    370                 375                 380

Leu Leu Ala Glu Asp Leu Pro Gly Thr Glu Asp Phe Val Gly His Gln
385                 390                 395                 400

Gly Thr Val Pro Ser Asp Asn Ile Asp Ser Pro Gly Arg Asn Ala Ser
                405                 410                 415

Thr Asn Asp Ser Leu Leu
            420

<210> SEQ ID NO 9
<211> LENGTH: 288
<212> TYPE: PRT
<213> ORGANISM: Homo sapiens

<400> SEQUENCE: 9

Ser Met Ile Thr Ala Ile Thr Ile Met Ala Leu Tyr Ser Ile Val Cys
1               5                   10                  15

Val Val Gly Leu Phe Gly Asn Phe Leu Val Met Tyr Val Ile Val Arg
                20                  25                  30

Tyr Thr Lys Met Lys Thr Ala Thr Asn Ile Tyr Ile Phe Asn Leu Ala
            35                  40                  45

Leu Ala Asp Ala Leu Ala Thr Ser Thr Leu Pro Phe Gln Ser Val Asn
50                  55                  60

Tyr Leu Met Gly Thr Trp Pro Phe Gly Thr Ile Leu Cys Lys Ile Val
65                  70                  75                  80

Ile Ser Ile Asp Tyr Tyr Asn Met Phe Thr Ser Ile Phe Thr Leu Cys
                85                  90                  95

Thr Met Ser Val Asp Arg Tyr Ile Ala Val Cys His Pro Val Lys Ala
            100                 105                 110

Leu Asp Phe Arg Thr Pro Arg Asn Ala Lys Ile Ile Asn Val Cys Asn
        115                 120                 125

Trp Ile Leu Ser Ser Ala Ile Gly Leu Pro Val Met Phe Met Ala Thr
    130                 135                 140
```

```
Thr Lys Tyr Arg Gln Gly Ser Ile Asp Cys Thr Leu Thr Phe Ser His
145                 150                 155                 160

Pro Thr Trp Tyr Trp Glu Asn Leu Leu Lys Ile Cys Val Phe Ile Phe
            165                 170                 175

Ala Phe Ile Met Pro Val Leu Ile Ile Thr Val Cys Tyr Gly Leu Met
        180                 185                 190

Ile Leu Arg Leu Lys Ser Val Arg Met Leu Ser Gly Ser Lys Glu Lys
    195                 200                 205

Asp Arg Asn Leu Arg Arg Ile Thr Arg Met Val Leu Val Val Val Ala
210                 215                 220

Val Phe Ile Val Cys Trp Thr Pro Ile His Ile Tyr Val Ile Ile Lys
225                 230                 235                 240

Ala Leu Val Thr Ile Pro Glu Thr Thr Phe Gln Thr Val Ser Trp His
                245                 250                 255

Phe Cys Ile Ala Leu Gly Tyr Thr Asn Ser Cys Leu Asn Pro Val Leu
        260                 265                 270

Tyr Ala Phe Leu Asp Glu Asn Phe Lys Arg Cys Phe Arg Glu Phe Cys
    275                 280                 285

<210> SEQ ID NO 10
<211> LENGTH: 6
<212> TYPE: PRT
<213> ORGANISM: Mus sp.

<400> SEQUENCE: 10

Met Leu Ser Gly Ser Lys
1               5

<210> SEQ ID NO 11
<211> LENGTH: 413
<212> TYPE: PRT
<213> ORGANISM: Homo sapiens

<400> SEQUENCE: 11

Met Gly Gln Pro Gly Asn Gly Ser Ala Phe Leu Leu Ala Pro Asn Gly
1               5                   10                  15

Ser His Ala Pro Asp His Asp Val Thr Gln Glu Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
            85                  90                  95

Lys Met Trp Thr Phe Gly Asn Phe Trp Cys Glu Phe Trp Thr Ser Ile
        100                 105                 110

Asp Val Leu Cys Val Thr Ala Ser Ile Glu Thr Leu Cys Val Ile Ala
    115                 120                 125

Val Asp Arg Tyr Phe Ala Ile Thr Ser Pro Phe Lys Tyr Gln Ser Leu
130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
            165                 170                 175
```

-continued

```
Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
            195                 200                 205

Tyr Val Pro Leu Val Ile Met Val Phe Val Tyr Ser Arg Val Phe Gln
            210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
            245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
            275                 280                 285

Phe Phe Ile Val Asn Ile Val His Val Ile Gln Asp Asn Leu Ile Arg
            290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
            325                 330                 335

Gln Glu Leu Leu Cys Leu Arg Arg Ser Ser Leu Lys Ala Tyr Gly Asn
            340                 345                 350

Gly Tyr Ser Ser Asn Gly Asn Thr Gly Glu Gln Ser Gly Tyr His Val
            355                 360                 365

Glu Gln Glu Lys Glu Asn Lys Leu Leu Cys Glu Asp Leu Pro Gly Thr
            370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
            405                 410

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 12

His His His His His
1               5

<210> SEQ ID NO 13
<211> LENGTH: 16
<212> TYPE: PRT
<213> ORGANISM: Unknown
<220> FEATURE:
<223> OTHER INFORMATION: Description of Unknown: bovine rhodopsin
      peptide

<400> SEQUENCE: 13

Ser Leu Val Val Leu Ala Ile Glu Arg Tyr Val Val Val Cys Lys Pro
1               5                   10                  15

<210> SEQ ID NO 14
<211> LENGTH: 16
<212> TYPE: PRT
<213> ORGANISM: Unknown
<220> FEATURE:
```

```
<223> OTHER INFORMATION: Description of Unknown: beta-2 adrenergic
      receptor peptide

<400> SEQUENCE: 14

Thr Leu Cys Val Ile Ala Val Asp Arg Tyr Phe Ala Ile Thr Ser Pro
1               5                   10                  15

<210> SEQ ID NO 15
<211> LENGTH: 16
<212> TYPE: PRT
<213> ORGANISM: Unknown
<220> FEATURE:
<223> OTHER INFORMATION: Description of Unknown: MUR peptide

<400> SEQUENCE: 15

Thr Leu Cys Thr Met Ser Val Asp Arg Tyr Ile Ala Val Cys His Pro
1               5                   10                  15

<210> SEQ ID NO 16
<211> LENGTH: 288
<212> TYPE: PRT
<213> ORGANISM: Mus sp.

<400> SEQUENCE: 16

Met Val Thr Ala Ile Thr Ile Met Ala Leu Tyr Ser Ile Val Cys Val
1               5                   10                  15

Val Gly Leu Phe Gly Asn Phe Leu Val Met Tyr Val Ile Val Arg Tyr
                20                  25                  30

Thr Lys Met Lys Thr Ala Thr Asn Ile Tyr Ile Phe Asn Leu Ala Leu
            35                  40                  45

Ala Asp Ala Leu Ala Thr Ser Thr Leu Pro Phe Gln Ser Val Asn Tyr
        50                  55                  60

Leu Met Gly Thr Trp Pro Phe Gly Asn Ile Leu Cys Lys Ile Val Ile
65                  70                  75                  80

Ser Ile Asp Tyr Tyr Asn Met Phe Thr Ser Ile Phe Thr Leu Cys Thr
                85                  90                  95

Met Ser Val Asp Arg Tyr Ile Ala Val Cys His Pro Val Lys Ala Leu
            100                 105                 110

Asp Phe Arg Thr Pro Arg Asn Ala Lys Ile Val Asn Val Cys Asn Trp
        115                 120                 125

Ile Leu Ser Ser Ala Ile Gly Leu Pro Val Met Phe Met Ala Thr Thr
130                 135                 140

Lys Tyr Arg Gln Gly Ser Ile Asp Cys Thr Leu Thr Phe Ser His Pro
145                 150                 155                 160

Thr Trp Tyr Trp Glu Asn Leu Leu Lys Ile Cys Val Phe Ile Phe Ala
                165                 170                 175

Phe Ile Met Pro Val Leu Ile Ile Thr Val Cys Tyr Gly Leu Met Ile
            180                 185                 190

Leu Arg Leu Lys Ser Val Arg Met Leu Ser Gly Ser Lys Glu Lys Asp
        195                 200                 205

Arg Asn Leu Arg Arg Ile Thr Arg Met Val Leu Val Val Val Ala Val
        210                 215                 220

Phe Ile Val Cys Trp Thr Pro Ile His Ile Tyr Val Ile Ile Lys Ala
225                 230                 235                 240

Leu Ile Thr Ile Pro Glu Thr Thr Phe Gln Thr Val Ser Trp His Phe
                245                 250                 255

Cys Ile Ala Leu Gly Tyr Thr Asn Ser Cys Leu Asn Pro Val Leu Tyr
            260                 265                 270
```

-continued

```
Ala Phe Leu Asp Glu Asn Phe Lys Arg Cys Phe Arg Glu Phe Cys Ile
        275                 280                 285
```